(12) United States Patent
Fox et al.

(10) Patent No.: US 9,770,679 B2
(45) Date of Patent: Sep. 26, 2017

(54) SEQUENTIAL CENTRIFUGE

(71) Applicant: TRIPATH IMAGING, INC., Burlington, NC (US)

(72) Inventors: William Alan Fox, Burlington, NC (US); Charles L. Carrico, Burlington, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 179 days.

(21) Appl. No.: 14/857,492

(22) Filed: Sep. 17, 2015

(65) Prior Publication Data

US 2016/0008745 A1  Jan. 14, 2016

Related U.S. Application Data

(62) Division of application No. 12/747,460, filed as application No. PCT/US2008/086145 on Dec. 10, 2008, now Pat. No. 9,211,549.

(Continued)

(51) Int. Cl.
| | |
|---|---|
| *B04B 13/00* | (2006.01) |
| *B01D 21/26* | (2006.01) |
| *B04B 11/04* | (2006.01) |
| *B04B 5/04* | (2006.01) |
| *G01N 35/00* | (2006.01) |

(52) U.S. Cl.
CPC .......... *B01D 21/262* (2013.01); *B04B 5/0414* (2013.01); *B04B 11/04* (2013.01); *B04B 13/00* (2013.01); *B04B 2011/046* (2013.01); *G01N 2035/00504* (2013.01)

(58) Field of Classification Search
CPC ......... B04B 9/10; B04B 11/04; B04B 11/043; B04B 13/00; B04B 2011/046
See application file for complete search history.

(56) References Cited

U.S. PATENT DOCUMENTS

| | | | |
|---|---|---|---|
| 3,151,073 A | 9/1964 | Anthon | |
| 3,587,676 A | 6/1971 | Oehlin et al. | |

(Continued)

FOREIGN PATENT DOCUMENTS

| | | |
|---|---|---|
| GB | 1 326 067 A | 8/1973 |
| WO | WO 00/49557 A2 | 8/2000 |

OTHER PUBLICATIONS

International Search Report for International Application No. PCT/US2008/086145, dated Mar. 27, 2009.

(Continued)

*Primary Examiner* — Timothy Cleveland
(74) *Attorney, Agent, or Firm* — Botos Churchill IP Law LLP

(57) ABSTRACT

The invention provides a sequential centrifuge for centrifuging discrete samples. Methods of more efficiently centrifuging discrete samples sequentially are also provided. The apparatus and methods for sequentially centrifuging discrete samples provide improved operating efficiencies over conventional batch centrifuges. Such advantages include reducing dwell time, increasing system throughput, reducing sample processing system footprint, and improving precision of the analytical process. The sequential centrifuge further provides the capability of handling critical samples without compromising the operating efficiencies achieved in centrifuging discrete samples in a sequential manner.

7 Claims, 16 Drawing Sheets

Related U.S. Application Data

(60) Provisional application No. 61/012,891, filed on Dec. 11, 2007.

(56) References Cited

U.S. PATENT DOCUMENTS

| | | | |
|---|---|---|---|
| 3,722,790 A | 3/1973 | Natelson | |
| 3,826,622 A | 7/1974 | Natelson | |
| 3,902,660 A | 9/1975 | Barber | |
| 3,944,188 A | 3/1976 | Parker et al. | |
| 4,058,252 A | 11/1977 | Williams | |
| 4,117,728 A | 10/1978 | Johnson | |
| 4,244,513 A | 1/1981 | Fayer et al. | |
| 4,266,505 A | 5/1981 | Bacus | |
| 4,276,258 A | 6/1981 | Ginsberg et al. | |
| 4,369,655 A | 1/1983 | Scearce | |
| 4,412,831 A | 11/1983 | Avery et al. | |
| 4,647,432 A | 3/1987 | Wakatake | |
| 4,708,940 A | 11/1987 | Yoshida et al. | |
| 4,800,164 A | 1/1989 | Bisconte | |
| 4,830,832 A | 5/1989 | Arpagaus et al. | |
| 4,847,205 A | 7/1989 | Burtis et al. | |
| 4,868,128 A | 9/1989 | Sommer et al. | |
| 5,166,889 A | 11/1992 | Cloyd | |
| 5,389,339 A | 2/1995 | Petschek et al. | |
| 5,480,378 A | 1/1996 | Weis-Fogh et al. | |
| 5,482,861 A | 1/1996 | Clark et al. | |
| 5,525,240 A | 6/1996 | Lemelson | |
| 5,592,948 A | 1/1997 | Gatten | |
| 5,620,660 A | 4/1997 | Belgardt et al. | |
| 5,769,775 A | 6/1998 | Quinlan et al. | |
| 5,814,276 A | 9/1998 | Riggs | |
| 6,060,022 A | 5/2000 | Pang et al. | |
| 6,374,982 B1 | 4/2002 | Cohen et al. | |
| 6,468,764 B1 | 10/2002 | Gibbs et al. | |
| 6,499,366 B1 | 12/2002 | Meadows et al. | |
| 6,547,140 B2 | 4/2003 | Marchand | |
| 6,634,557 B2 | 10/2003 | Kocznar et al. | |
| 6,635,007 B2 | 10/2003 | Evans, III et al. | |
| 6,721,615 B2 | 4/2004 | Fava et al. | |
| 6,769,316 B2 | 8/2004 | Rogers et al. | |
| 6,832,980 B2 | 12/2004 | Hayasaka | |
| 6,902,703 B2 | 6/2005 | Marquiss et al. | |
| 6,945,129 B2 | 9/2005 | Escal | |
| 7,008,788 B2 | 3/2006 | Schremp et al. | |
| 7,025,714 B2 | 4/2006 | Escal | |
| 7,091,864 B2 | 8/2006 | Veitch et al. | |
| 7,112,303 B2 | 9/2006 | Itoh | |
| 7,115,090 B2 | 10/2006 | Lagarde | |
| 7,255,669 B2 | 8/2007 | Shimizu et al. | |
| 7,258,840 B2 | 8/2007 | van der Maas et al. | |
| 7,275,682 B2 | 10/2007 | Excoffier et al. | |
| 2002/0132354 A1 | 9/2002 | Downs et al. | |
| 2003/0022176 A1 | 1/2003 | Schremp et al. | |
| 2003/0040117 A1 | 2/2003 | Devlin, Sr. | |
| 2003/0091473 A1 | 5/2003 | Downs et al. | |
| 2004/0014228 A1 | 1/2004 | Brignac, Jr. et al. | |
| 2004/0258565 A1 | 12/2004 | Watari | |
| 2005/0186113 A1 | 8/2005 | Koike et al. | |
| 2006/0051241 A1 | 3/2006 | Higuchi et al. | |
| 2006/0073510 A1 | 4/2006 | Fox et al. | |
| 2006/0159587 A1 | 7/2006 | Fechtner et al. | |
| 2006/0199916 A1 | 9/2006 | Van Es et al. | |
| 2006/0210435 A1 | 9/2006 | Alavie et al. | |
| 2007/0166194 A1 | 7/2007 | Wakatake | |
| 2009/0054222 A1 | 2/2009 | Zhang et al. | |

OTHER PUBLICATIONS

International Preliminary Report on Patentability and Written Opinion for International Application No. PCT/US2008/086145, dated Mar. 27, 2009.

International Search Report and Written Opinion for International Application No. PCT/US2009/036637 mailed Nov. 27, 2009.

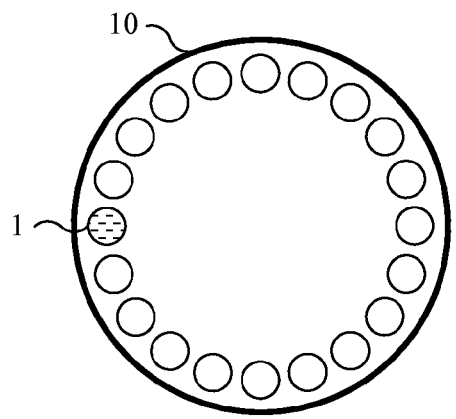
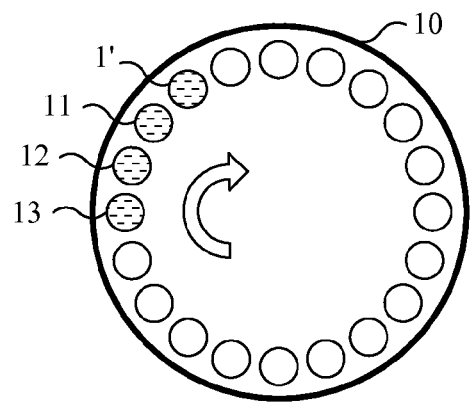
FIG. 9A       FIG. 9B
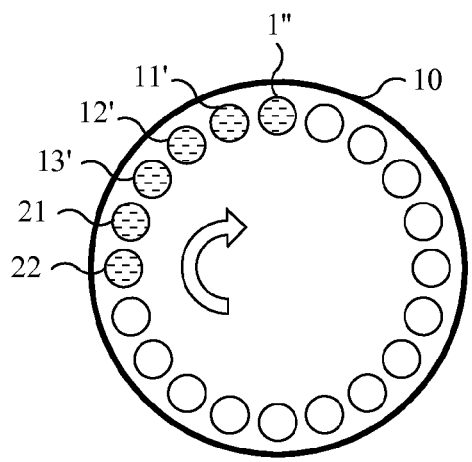
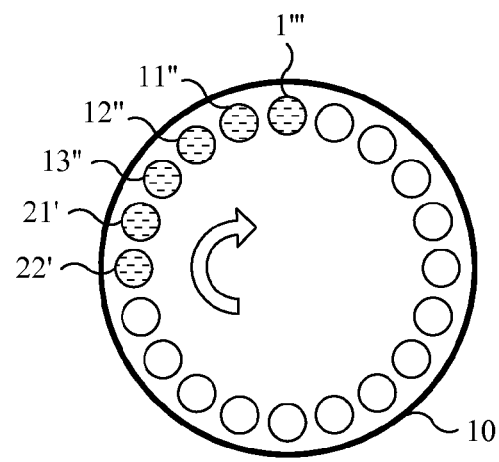
FIG. 9C       FIG. 9D

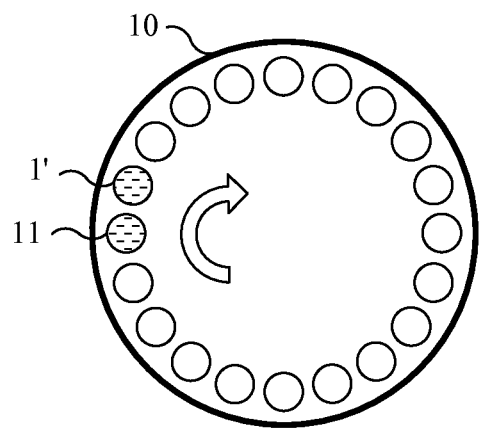
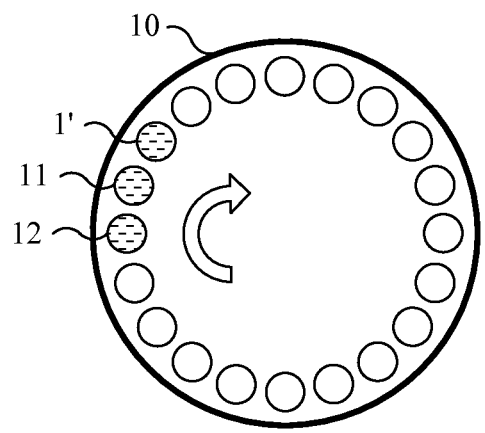
FIG. 10A    FIG. 10B
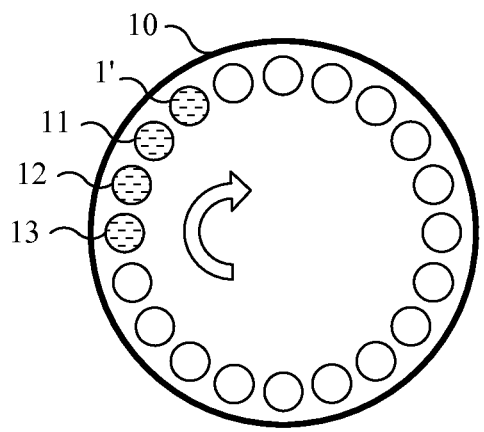
FIG. 10C

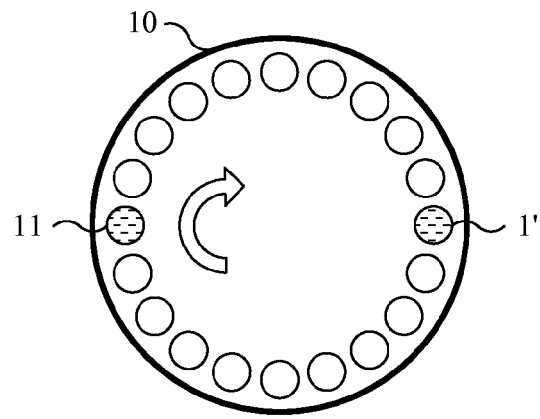
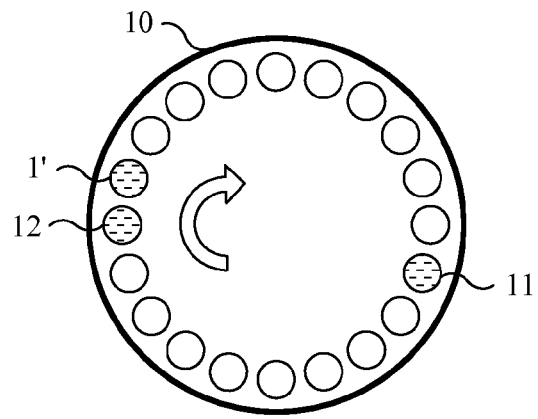
FIG. 12A      FIG. 12B
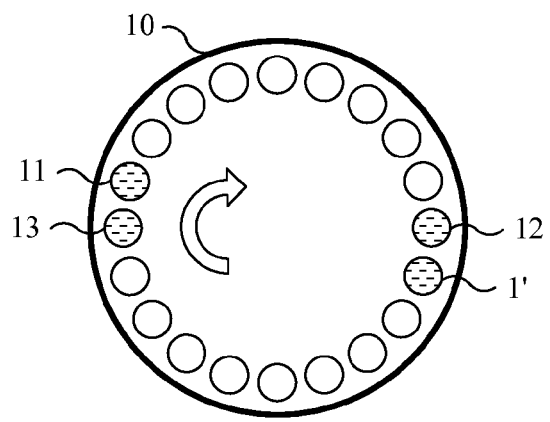
FIG. 12C

SEQUENTIAL CENTRIFUGE

CROSS-REFERENCE TO RELATED APPLICATIONS

This application is a divisional application of U.S. application Ser. No. 12/747,460, filed Sep. 14, 2010, which is a U.S National Phase under 35 U.S.C §371 of International Application PCT/US2008/086145, filed Dec. 10, 2008, which claims priority to U.S. Provisional Application No. 61/012,891, filed Dec. 11, 2007, each of which is incorporated herein in its entirety by reference.

FIELD OF INVENTION

The present invention relates to the art of automatic centrifugation. In particular, this invention relates to an apparatus for a sequential centrifuge to process discrete samples and methods of using the same.

BACKGROUND OF THE INVENTION

The centrifuge is typically used for processing samples in the chemical, biological, and medical sciences when such samples need to be separated into at least two constituent components each having varying densities and/or sedimentary rates. A centrifuge is used to isolate particles in suspended state from the medium in which they are held. Many research and clinical applications rely on the isolation of cells, subcellular organelles, and macromolecules typically from samples that need to be individually processed.

A laboratory centrifuge fundamentally consists of a container, tube, or vial for holding a specimen or sample, the container, tube, or vial designed such that it is capable of withstanding the sizeable forces applied by the centrifuge; a sample holder such as, for example, a tub-shaped bowel, carousel, or bucket for holding a plurality of containers, tubes, or vials; a rotor that retains at least one sample holder; a shaft upon which the rotor is mounted; a motor for turning the shaft that simultaneously spins the rotor and the at least one sample holder rotatably attached thereto; optionally, a lid affixed to a centrifuge housing containing the sample holder, the rotor, the shaft, and the motor; and a motor speed controller for achieving a desired relative centrifugal force (RCF). Some centrifuges are also equipped with controllers that have conventionally been used to ensure the lid is properly affixed to the centrifuge housing, precisely employ a set time and RCF on a batch of samples, and to alert the operator the centrifuge is out of balance if the unit has been equipped with an imbalance detection system. The shaft is driven at an application dependent selected speed that can be as high as 10,000 revolutions-per-minute (RPM) or more.

The centrifuge subjects the samples to a centrifugal force. The amount of centrifugal force is directly proportional to the mass of the sample, the distance the sample is from the spin axis, and the angular velocity or spin rate squared. The effect of the applied centrifugal force is to impose a separation force on a sample that is typically orders of magnitude greater than gravity at the earth's surface, which causes the sample to separate into its multidensity components much more quickly and effectively than if not subjected to the added force.

There are two primary types of centrifugal separations—differential separation, which relies primarily on the size differences of suspended particles, and density gradient centrifugation, which is carried out in at least one layer of gradient medium added to the sample container. The cell medium in density gradient centrifugation may be selected to prefer distributions based on particle size, density, and any combination thereof. Further, there are multiple types of rotors that can typically be classified into three common categories—swinging bucket, fixed-angle, and vertical—each of which generally identifies the position of the sample tubes during rotation.

Certain analyses require precise centrifugation conditions. For example, a blood sample must be separated into its constituent parts—plasma and blood cells—for subsequent analysis. The degree of centrifugation imposed on a sample is termed RCF. RCF is proportional to the radius of the rotor and the square of the angular velocity or speed of the centrifuge, measured by RPM. The calculation for applied RCF may have to be adjusted depending on the type of rotor used in the centrifuge. The RCF measures how many times a unit of gravity, or "g-force", is imposed on a processed sample. RCF is a ratio, in essence, of the applied centrifugal force relative to gravity.

Another parameter that is important to the overall degree of separation is the length of time a certain RCF is applied to a sample or also known as the total amount of force and time (F×T) or total FT that is applied to the sample. Failure to consistently apply the requisite RCF and centrifugation time to a particular sample can distort the final analysis of the separated material possibly rendering the results, for the most part, meaningless. Varying acceleration and deceleration profiles that contribute to the total FT can also impact the repeatability of results on separated samples.

Laboratory and/or clinical centrifugations conventionally are batch processes with most centrifuges designed to process multiple samples at once. When processing multiple, discrete samples, there is a delay in processing earlier samples placed into the centrifuge. This delay is known as dwell time. Furthermore, there must be sufficient samples available to fill the centrifuge or at least there must be enough samples to load the centrifuge in such a way that the centrifuge remains in balance about its rotational axis once centrifugation begins. The centrifuge may have static imbalances, dynamic imbalances, and any combination thereof. Static imbalances result from asymmetrical distributions of mass within the centrifuge. Dynamic imbalances may occur as variations in distribution of densities begin to occur throughout the samples that are being centrifuged. Operating a centrifuge that is not balanced can result in increased noise, incorrect final sample analysis because of the failure to achieve a requisite consistent RCF or because of possible sample resuspension as the rotation of the centrifuge moves through resonance peaks, and excessive vibration and machine movement possibly leading to damage or even full inoperability of the centrifuge unit. Further, batch centrifugation units are not amenable to efficiently processing critical specimens that arrive randomly but require quick turnaround analyses.

The extent of the idle time of a batch system capable of processing N samples but remaining idle until at least L samples are accumulated, with such samples arriving randomly to the batch system, has been addressed by Mathias A Dümmler and Alexander K. Schömig, "Using Discrete-Time Analysis in the Performance Evaluation of Manufacturing Systems" (paper presented at the annual International Conference on Semiconductor Manufacturing Operational Modeling and Simulation Meeting, San Francisco, Jan. 18-20, 1999). The amount of idle time is dependent upon both the number of samples, if any, remaining in the queue after the $n^{th}$ centrifugation starts and the number of samples arriving while the $n^{th}$ centrifugation is underway. The distribution of the number of samples remaining in the queue after the centrifugation has begun, $y_n(k)$, is given by:

$$y_n(k) = \begin{cases} 0, & k < n-1 \\ \sum_{i=-\infty}^{n-1} \max(0, x_{n-1}(i) - K), & k = n-1 \\ \max(0, x_{n-1}(k) - K), & k > n-1 \end{cases}$$

where the probability distribution of all prior samples waiting to be processed as they have accumulated at the end of the last centrifugation, $x_{n-1}(k)$ is represented by:

$$y_n = \max(0, x_{n-1} - K)$$

and $$K = L + \min(\max(0, x_{-1} - L), N - L).$$

I.e., if the number of samples in the queue to be loaded just prior to the $n^{th}$ centrifugation is greater than the number of samples that can be loaded, then these samples will wait to be loaded in the next centrifugation sequence. If there are an insufficient number of samples to either fill the centrifuge or meet the minimum required number of samples to maintain balance in the centrifuge, then there will be idle time in the operation of the centrifuge until a sufficient additional number of samples become available for processing.

Assuming geometrically distributed arrival times, the distribution of the number of samples arriving during any $n^{th}$ period of operation of the centrifuge, $\gamma_n(k)$, is given by:

$$\gamma_n(k) = \sum_{m=k}^{\infty} \binom{m}{k} p^k (1-p)^{m-k} b_n(m)$$

where $b_n(m)$ is the distribution along the length of the $n^{th}$ centrifugation period and p is the probability of a sample arriving at any point in time.

The probability distribution of two random variables is given by the convolution theorem. Hence, the probability distribution for the number of samples waiting to be loaded after the $n^{th}$ centrifugation, $x_n(k)$, is given by:

$$x_n(k) = y_n(k) \otimes \gamma_n(k) = \sum_{l=-\infty}^{\infty} y_n(l) \cdot \gamma_n(k-l).$$

I.e., the number of samples waiting to be loaded after the $n^{th}$ centrifugation for the next $n+1^{th}$ centrifugation is dependent on the number of samples remaining in the queue to be processed, if any, just prior to starting the $n^{th}$ centrifugation sequence and the number of samples that have arrived while the $n^{th}$ centrifugation is underway.

The mean time samples must wait before being centrifuged, $\overline{W}$, is given by Little's law:

$$\overline{W} = \overline{Q}/\overline{R}$$

where $\overline{Q}$ is the mean number of samples in the queue at the start of centrifugation given by:

$$\overline{Q} = \Sigma i \cdot x_n(i)$$

and $\overline{R}$ is the average arrival rate of the samples.

Based on Little's formula, the mean waiting time of the samples before being centrifuged, $\overline{W}$, is minimized when there are consistently no samples waiting to be processed at the start of any centrifugation as long as there are at least a sufficient number of samples, L, already loaded to maintain balance in the centrifuge.

The study provides revealing mathematical insight, using discrete time analysis, into the problems surrounding the potential limitations on batch processing in discrete time processing systems. As the analysis confirms, where the probability of appearance of a sample is reasonably consistent, then a centrifuge can be sized such that the idle time resulting from waiting for the requisite number of samples to arrive before centrifugation can begin can be minimized. Indeed, where such probabilities are known, the centrifuge can be sized such that there are a sufficient number of samples to fill the centrifuge without any idle time between each batch centrifugation sequence and any samples remaining at the end of a given period. However, such consistent probabilities in the clinical setting are rare. There will inevitably be variability in the probability of sample arrivals. Such variability typically is inconsistent and difficult to estimate. Hence, a centrifuge in the clinical setting typically needs to be sized for those periods when the probability of arrival of a sample is greatest in order to keep up with demand in those peak periods. Inevitably, this will lead to increased idle time when the probability of arrival of a sample is anything less than the maximum probability for which the centrifuge has been designed.

An alternative for laboratories that must process samples having varying probabilities of arrival of samples is to purchase additional centrifuges each having smaller capacities, but this comes at increased capital expenditure and operating costs. Even if a laboratory is willing to accept the increased costs for a multiple number of centrifuges, while idle time can be reduced, some amount of idle time will always remain as long as the probability for the arrival of a sample varies from the probabilities used in the design of the centrifuges.

Advancements have been made, for example, in the clinical laboratory to streamline sample processing and reduce the amount of sample that is needed on which to perform an analysis. The need to gain even further efficiency improvements from the centrifugation process has been recognized in the art. For example, U.S. Pat. No. 4,058,252 entitled "Automatic Sample Processing Apparatus" to Williams discloses advancing a number of centrifugation units each having a plurality of containers mounted on a conveyor to various processing stations. U.S. Pat. No. 6,060,022 entitled "Automated Sample Processing System Including Automatic Centrifuge Device" to Pang et al. discloses a centrifugation subsystem that involves loading containers to be processed in a plurality of buckets, checking that the buckets are in balance, loading the buckets into the centrifuge, centrifuging, and unloading the buckets from the centrifuge. However, these systems are limited since the sample holders must be balanced before they are placed in the centrifuge—a process that can prove to be time consuming. Centrifugation cannot begin until at least a minimum number of samples have been loaded such that the centrifugation units or buckets can maintain balance in the centrifuge. These batch processing systems will have idle times that can be determined by the discrete time analysis disclosed herein.

Automated loading and unloading procedures of samples by robotics are disclosed in, for example, U.S. Pat. No. 5,166,889 entitled "Robotic Liquid Sampling System" to Cloyd, U.S. Pat. No. 5,769,775 entitled "Automated Centrifuge for Automatically Receiving and Balancing Samples" to Quinlan, and U.S. Pat. No. 6,374,982 entitled "Robotics for Transporting Containers and Objects within an Automated Analytic Instrument and Service Tool for Servicing Robots" to Cohen et al. However, these automated processing techniques still require that some or all of the preliminary and subsequent sample processing steps be suspended or withheld until centrifugation is complete on the batch of samples being processed in the centrifuge.

Advances have also been made with respect to the need to balance centrifuges that process varying numbers of samples and samples that have varying amounts of a specimen to be processed. U.S. Pat. No. 5,769,775 to Quinlan discloses a method of determining an arrangement of a preselected number of sample racks each holding a plurality of containers with samples that are to be loaded in the centrifuge such that the unit will remain in balance in a given certain threshold. As further disclosed, the system may also have a weighing station for predetermining the proper weight distribution of the sample racks within the centrifuge, similar to the weighing station and plurality of buckets disclosed in U.S. Pat. No. 6,060,022. The methods that are the subject of these disclosures require that the centrifuge be balanced using a multitude of sample racks with a varying number of samples prior to centrifugation. The methodologies serve to potentially increase the idle time of the centrifuge depending on the extent of balancing and rebalancing of samples that is needed prior to loading the centrifuge with the sample racks or buckets.

Centrifuges can be manufactured to allow the unit to have more tolerance for off balance samples or even be self-balancing to some degree. For example, a centrifuge may have larger rotor bearings as disclosed in U.S. Pat. No. 5,769,775 or may have upper and lower bearing mounts that are capable of substantial movement in the horizontal plane for self-balancing as disclosed in U.S. Pat. No. 4,412,831 entitled "Two Plane Self-Balancing Centrifuge" to Avery et al. Conventionally, the self-balancing units seem to have been the less-favored approach since they increase the cost of the centrifuge, only serve to reduce the time for balancing samples prior to beginning centrifugation, and provide little, if any, efficiency gains during the batch centrifugation process. Such advantages have not been used to reduce the idle time of the centrifuge resulting from varying probabilities of arrival times of samples to be processed in the centrifuge.

A more automated system for controlling centrifuge balance is the subject of the disclosure in U.S. Pat. No. 6,635,007 entitled "Method and Apparatus for Detecting and Controlling Imbalance Conditions in a Centrifuge System" to Evans et al. A centrifuge imbalance is detected by an imbalance detection system that includes an accelerometer that measures longitudinal acceleration. When an imbalance is detected, a controller can automatically make adjustments to bring the centrifuge back into balance, though the disclosure is silent on what adjustments can be made. Admitting that centrifuge balancing is difficult to fully automate, U.S. Pat. No. 7,115,090 entitled "Method and Device for Pretreatment of Samples by Centrifuge" to Lagarde discloses a method that includes the steps of detecting the presence of tubes inside a container to be placed in the centrifuge, simulating the load of the centrifuge incorporating the container, selecting a suitable balancing container as needed, and removing the balancing container once centrifugation is complete.

While advancements have been made to streamline processing discrete samples in a centrifuge system and maintaining balance in the centrifuge system, there remains in the art a need to process a varying number of samples in a centrifuge while reducing, if not eliminating, the idle time of the unit resulting from the batch processing of samples. Further, the art requires that the centrifuge maintain balance about its rotational axis when processing such samples.

An additional need that remains in the art is the ability to process irregular critical samples that require priority handling without any substantial loss in efficiency of processing other discrete samples in the centrifuge system.

BRIEF SUMMARY OF THE INVENTION

The present invention relates to devices and methods for sequentially centrifuging discrete samples. Without intending to be bound by theory, the sequential processing techniques of the invention provide improved operational efficiencies over conventional batch centrifuges by reducing dwell time, limiting idle time, requiring smaller processing system footprints, and improving precision of the analytical process.

In one aspect, the invention provides a sequential centrifuge. The sequential centrifuge has a drive subsystem, a rotor rotatably coupled to the drive subsystem, and one or more sample holders affixed, optionally detachably affixed, to the rotor. The sample holder has a plurality of sample reservoirs that are capable of holding the discrete samples to be centrifuged.

The sequential centrifuge further comprises an indexing system that advances an index from a current available sample reservoir to a next available sample reservoir and a control system interfaced to the drive subsystem for performing a centrifugation sequence.

In certain embodiments of the invention, the sequential centrifuge has a transfer assembly for loading a sample into a sample reservoir. In other embodiments of the invention, the sequential centrifuge has an extraction assembly for removing a centrifuged sample that has achieved a desired total amount of relative centrifugal force (RCF) and centrifugation time, or total FT from the centrifuge.

Multiple embodiments of the invention are found in the way the centrifugation sequence is configured to operate. In one embodiment, the sequential centrifuge processes a new sample in each sequence, assuming there are remaining available reservoirs within the centrifuge. In one embodiment, the centrifugation sequence utilizes the indexing system to advance the index to the next available sample reservoir; an acceleration cycle increases the speed of the centrifuge to the desired RCF; the drive subsystem maintains a desired, preset RCF for a preset period of time during a centrifugation cycle; and a deceleration cycle brings the centrifuge to a stop. In another embodiment, the transfer assembly loads the sample into the current available sample reservoir. Generally, any time the centrifuge is stopped, any centrifuged sample that has achieved a desired total FT is removed from the centrifuge. In one embodiment of the invention, an extraction assembly removes the centrifuged sample from the centrifuge.

In another embodiment of the invention, the centrifugation sequence performs similar steps except that the centrifugation cycle maintains the desired, preset RCF until an event occurs. In one embodiment, the event includes at least one of a preset period of time has elapsed, a preset number of samples have become available for loading, a minimum period of time has elapsed, and a desired total FT is achieved by any of the centrifuged samples. In one embodiment of the invention, the preset number of samples is one sample. In another embodiment of the invention, the preset number of samples is more than one sample.

In other embodiments of the invention, the sample to be centrifuged is a critical sample and the centrifugation cycle is continued until any centrifuged sample, including the critical sample, has achieved a desired total FT. In another embodiment, the centrifugation cycle will stop to load a critical sample that becomes available for processing as long as there is room in the centrifuge to load the critical sample.

In certain embodiments of the invention, the centrifugation sequence is repeated until another sample is available for loading. However, any centrifuged sample that has achieved a desired total FT should be removed from the centrifuge.

The indexing system may be configured to index the next available sample reservoir to meet any number of objectives. The next available sample reservoir may be indexed to a sample reservoir that is next to the current available sample reservoir, a sample reservoir that is opposite to the current available sample reservoir, a sample reservoir needed to maintain balance in the centrifuge, or any other sample reservoir of the sample holder. In certain embodiments, the sample reservoir needed to maintain balance in the centrifuge may be, for instance, the sample reservoir next to the current available sample reservoir, the sample reservoir opposite to the current available sample reservoir, or any other sample reservoir available within the centrifuge. In certain embodiments, when the centrifuge has more than one sample holder, the indexing system may index reservoirs in any of the sample holders. In yet other embodiments, the indexing system may index reservoirs in other sequential centrifuges when more than one sequential centrifuge is in operation.

Another aspect of the invention provides methods of sequentially centrifuging a plurality of samples. One embodiment of the invention, provides a method of sequentially centrifuging a plurality of samples in a centrifuge comprising a drive subsystem, rotor coupled to the drive subsystem, and at least one sample holder affixed to the rotor, the at least one sample holder having a plurality of reservoirs for holding a sample. The steps of such a method include loading a first sample into a current available sample reservoir; indexing to a next available sample reservoir; accelerating to achieve a preset RCF; maintaining the preset RCF for an amount of time less than the amount of time needed to achieve a desired total FT for the first sample; decelerating to bring the centrifuge to a stop; repeating the loading and indexing steps for at least one other sample and the accelerating, maintaining, and decelerating steps until the first sample has achieved the desired total FT; and removing the first sample from the centrifuge.

In another embodiment of the invention, the method includes sequentially centrifuging a plurality of samples in a centrifuge comprising a drive subsystem, rotor coupled to the drive subsystem, and at least one sample holder affixed to the rotor, the at least one sample holder having a plurality of reservoirs for holding a sample. The steps of the method include loading the sample into a current available sample reservoir; indexing to a next available sample reservoir; accelerating to achieve a preset RCF; maintaining the preset RCF until an event occurs, the event selected from the group consisting of a preset period of time has elapsed, a preset number of samples have become available for loading, a minimum period of time has elapsed, a desired total FT is achieved by any centrifuged sample, and combinations thereof; decelerating to bring the centrifuge to a stop; and removing a centrifuged sample that has achieved the desired total FT.

In another embodiment of the invention, the method of sequentially centrifuging a plurality of samples involves continuously repeating the steps as provided until there are no remaining samples that are waiting to be loaded and no centrifuged sample remains in the centrifuge that has not achieved a desired total FT.

In another embodiment of the invention, the method of sequentially centrifuging a plurality of samples involves a sample that is a critical sample. Preferably, the critical sample is placed in front of a sample processing queue for immediate processing. In this embodiment of the invention, the step of maintaining the preset RCF until an event occurs, can include any of another critical sample is available at the front of the sample processing queue, the desired total FT is achieved by any one centrifuged sample, the desired total FT is achieved by the critical sample, and combinations thereof.

In another embodiment of the invention, the method includes the step of indexing to a next available sample reservoir that needs to be loaded in order to maintain balance in the sequential centrifuge.

BRIEF DESCRIPTION OF THE SEVERAL VIEWS OF THE DRAWINGS

Figure 1:
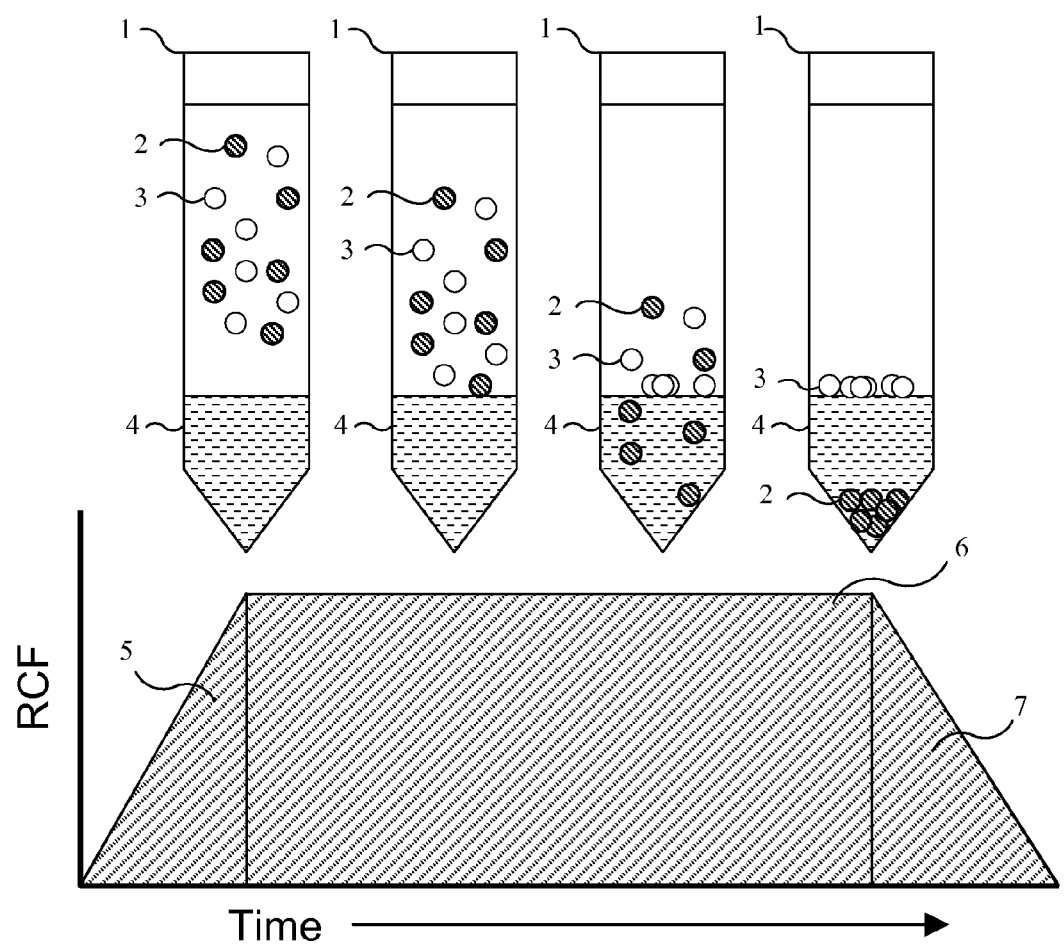
Figure 2:
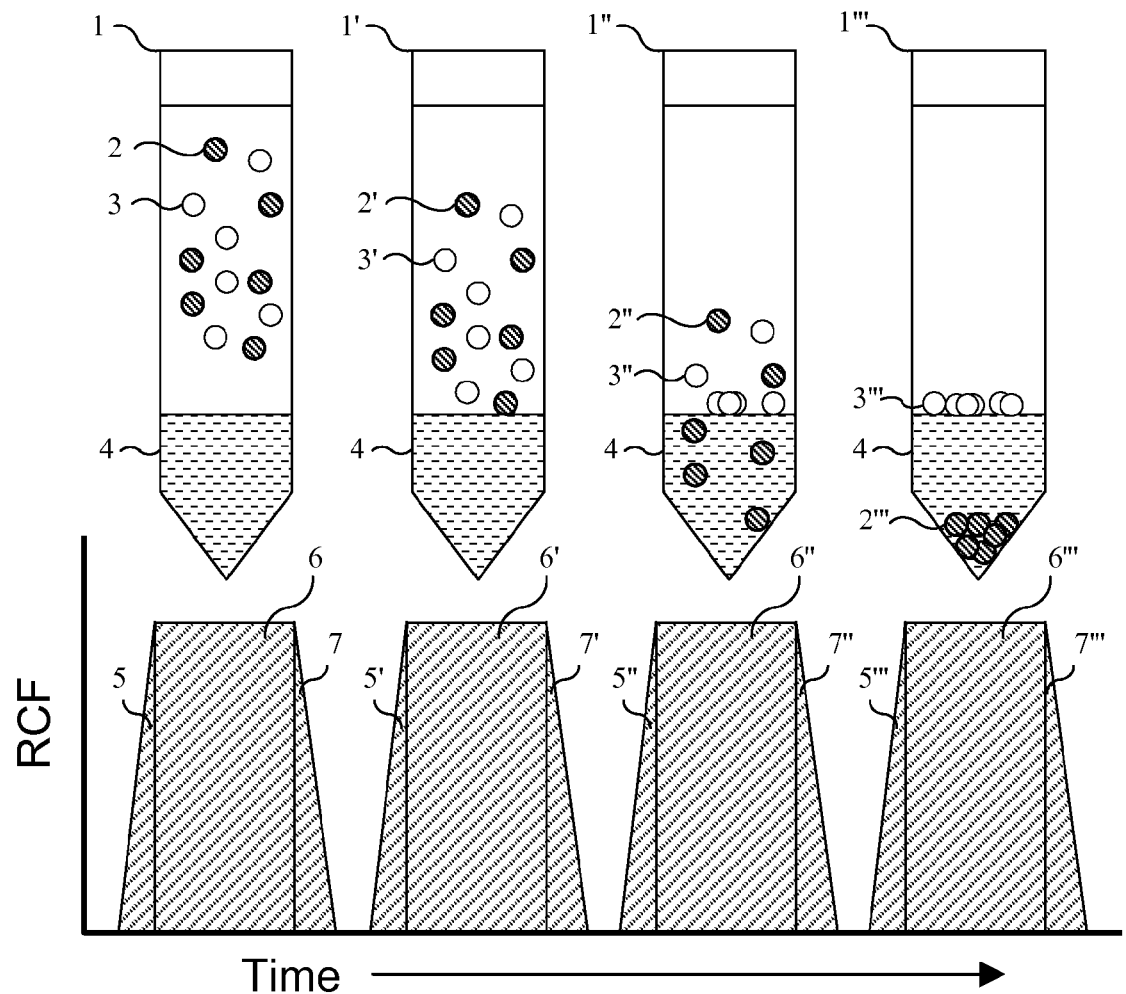
Figure 5:
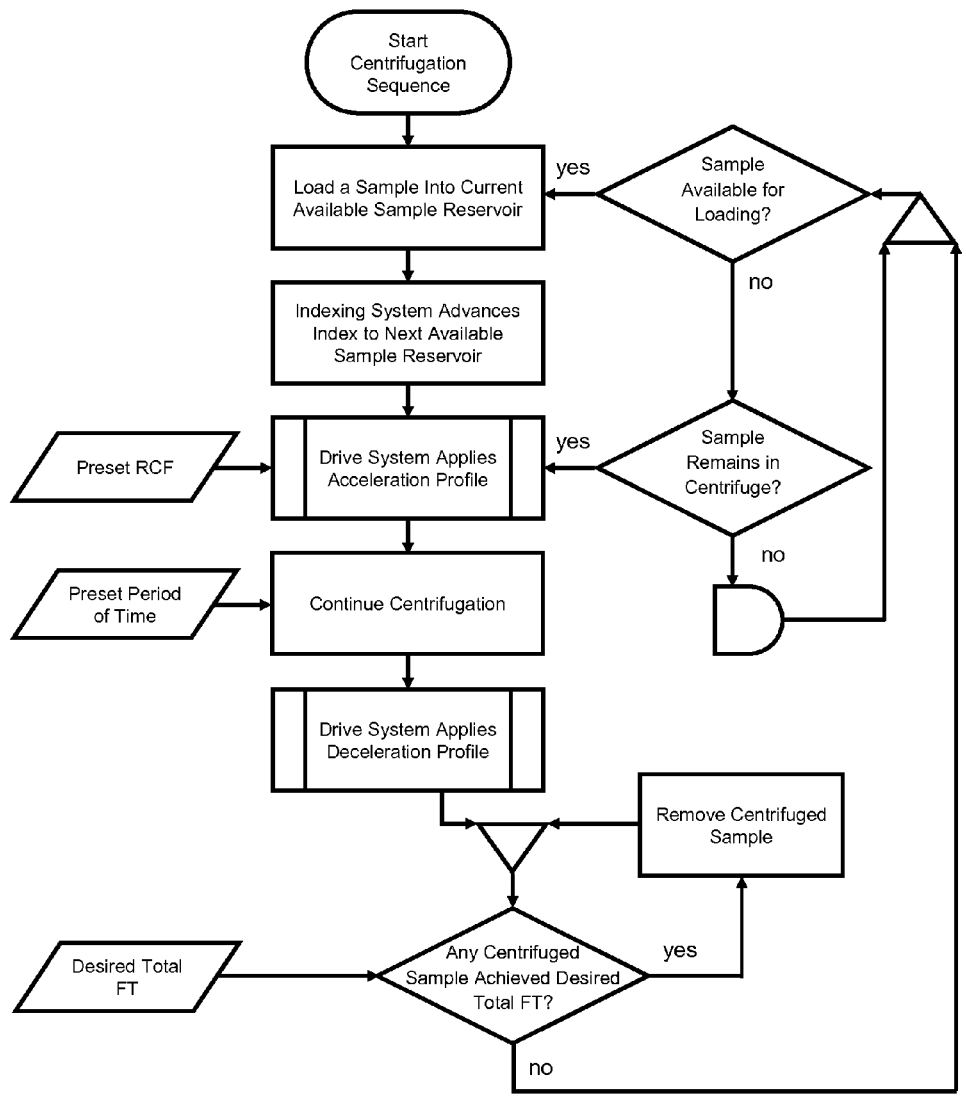
Figure 6:
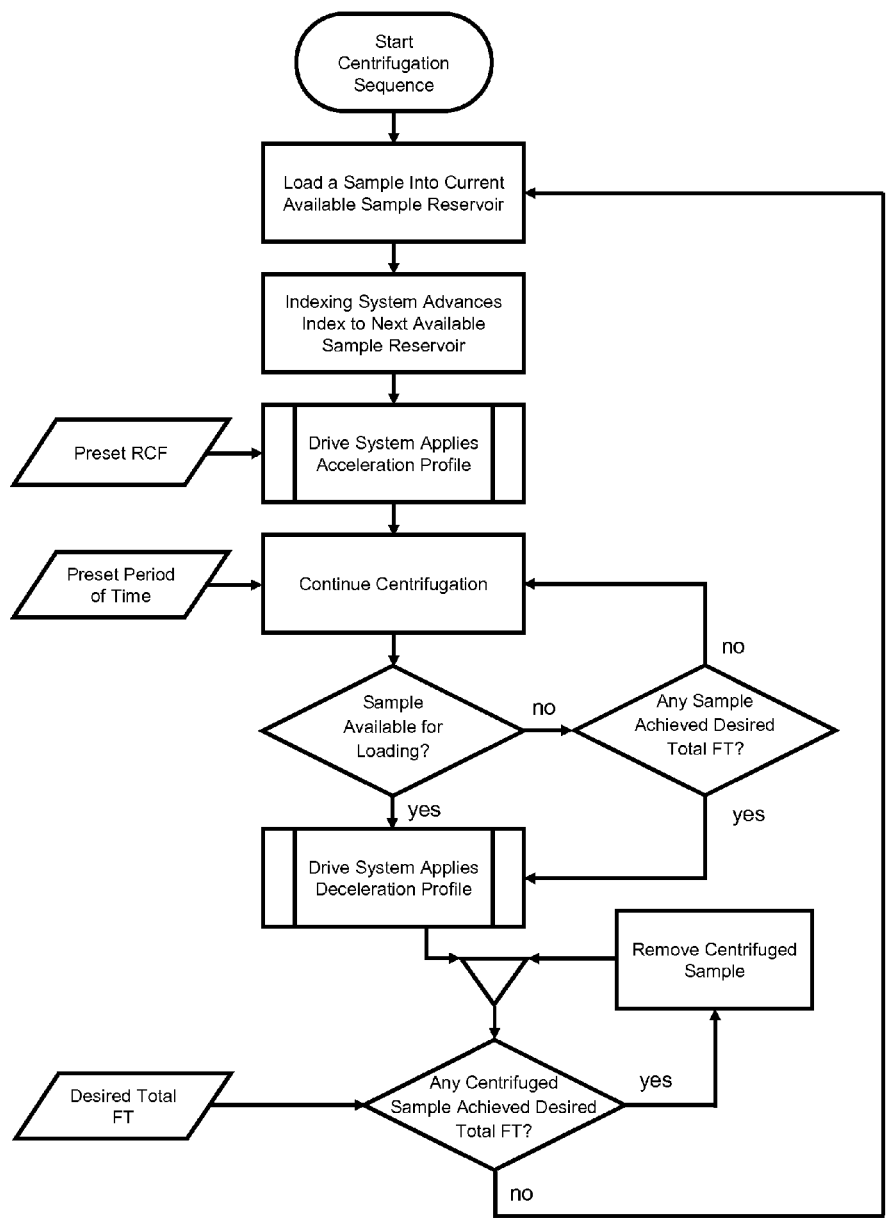
Figure 7:
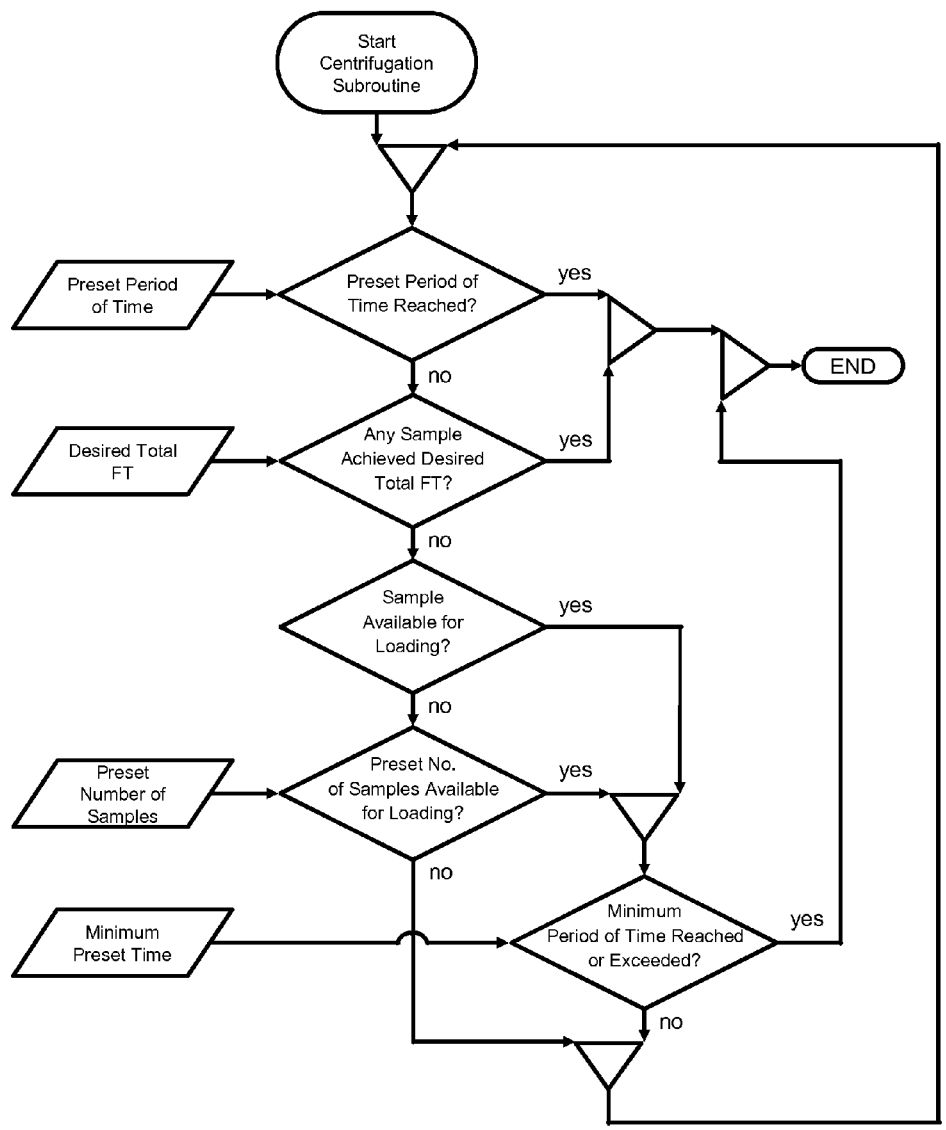
Figure 8:
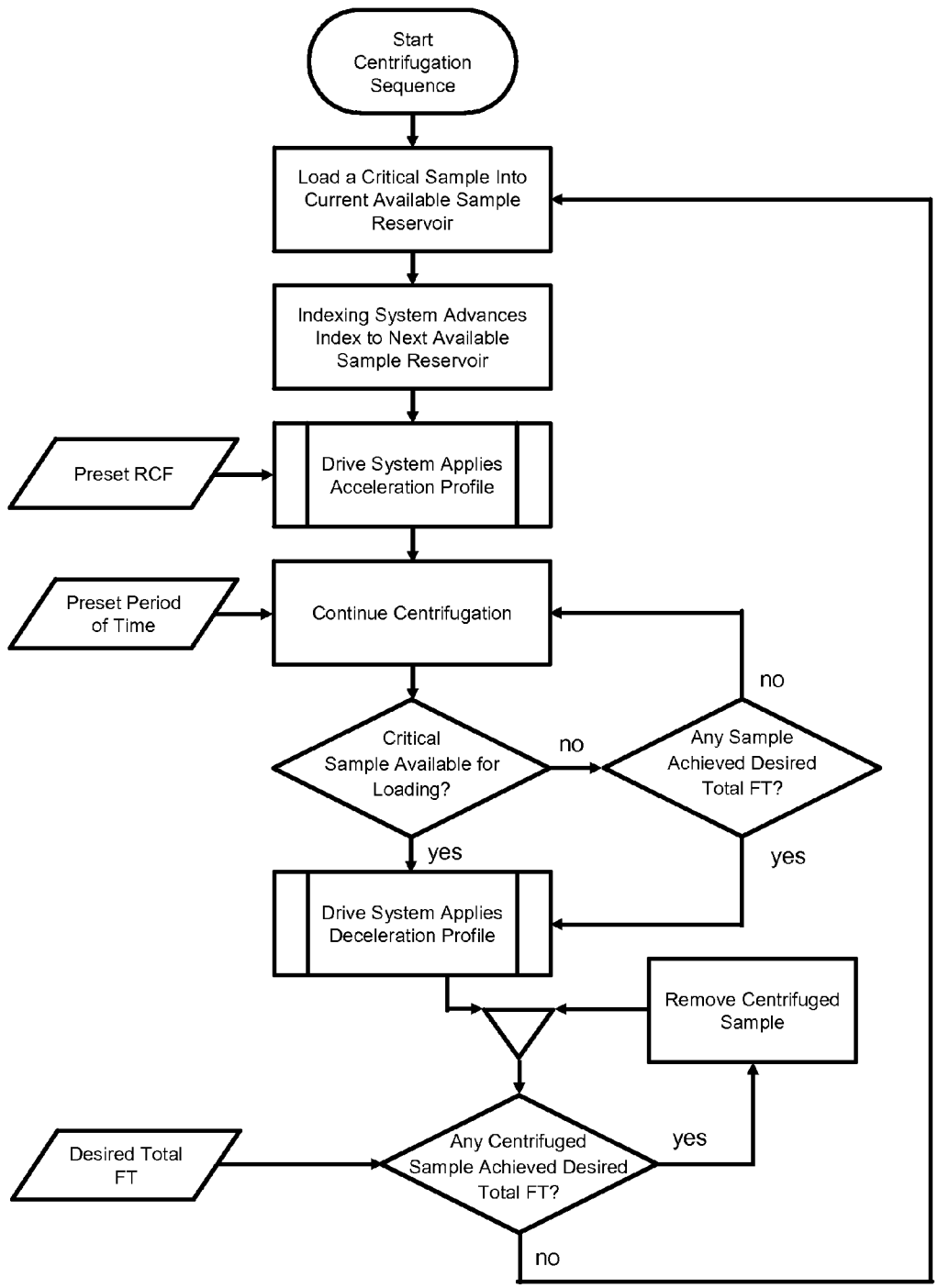
Figure 11A:
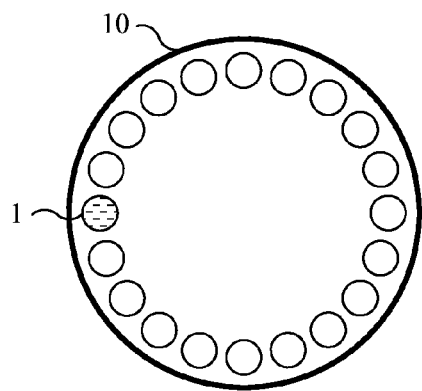
Figure 11B:
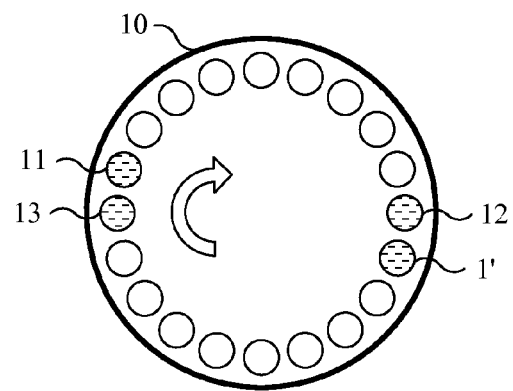
Figure 11C:
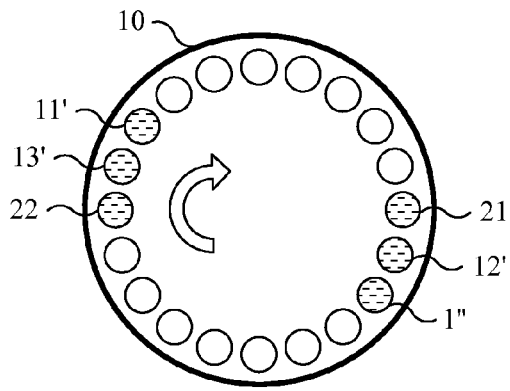
Figure 11D:
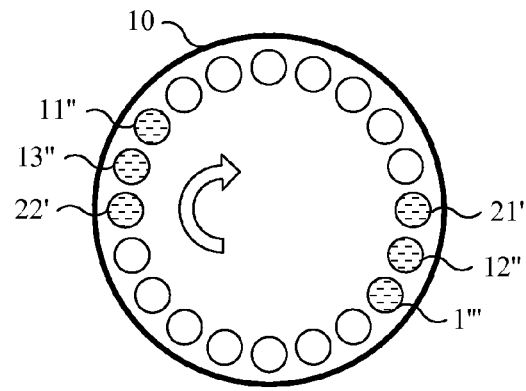
Figure 13:
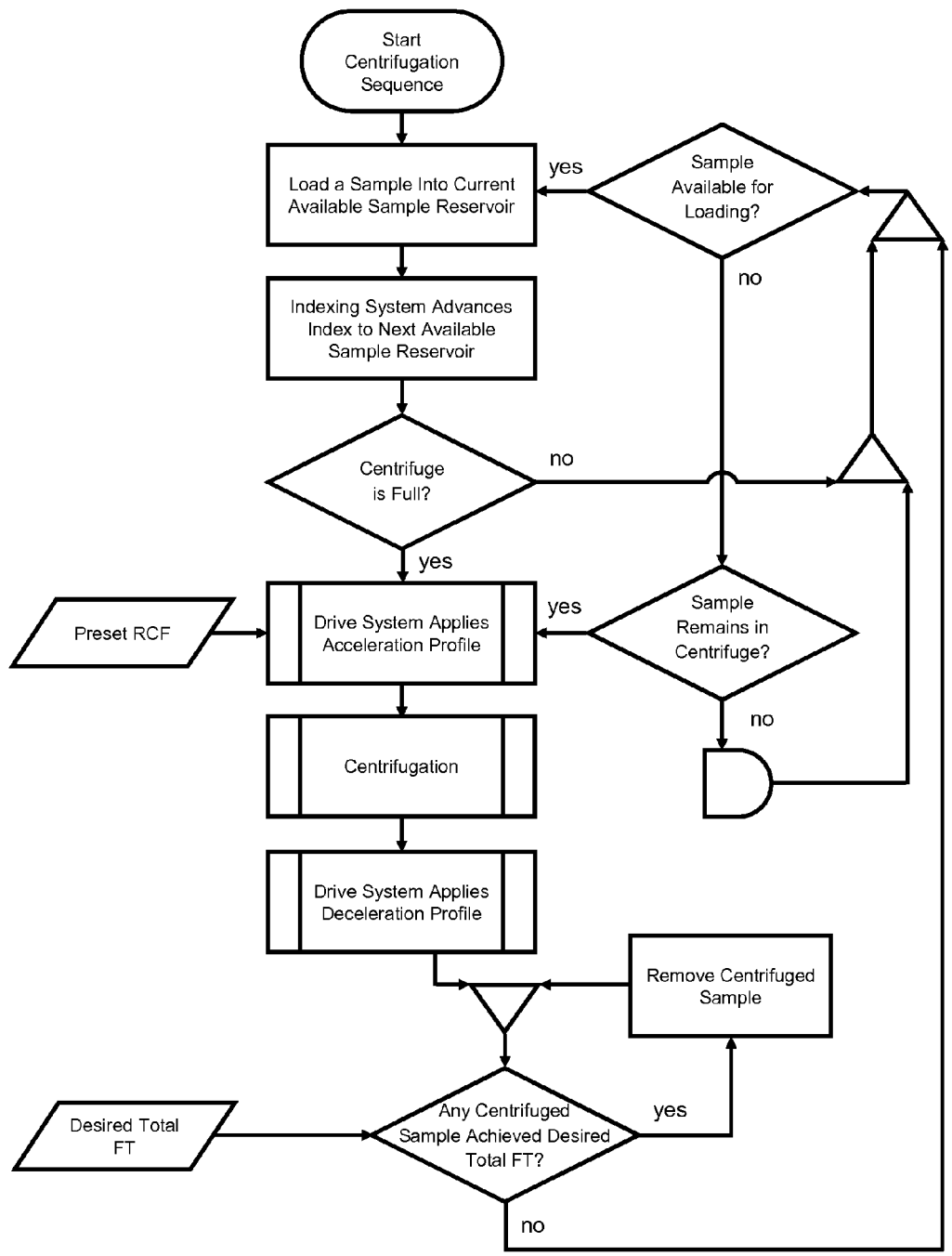
Figure 14:
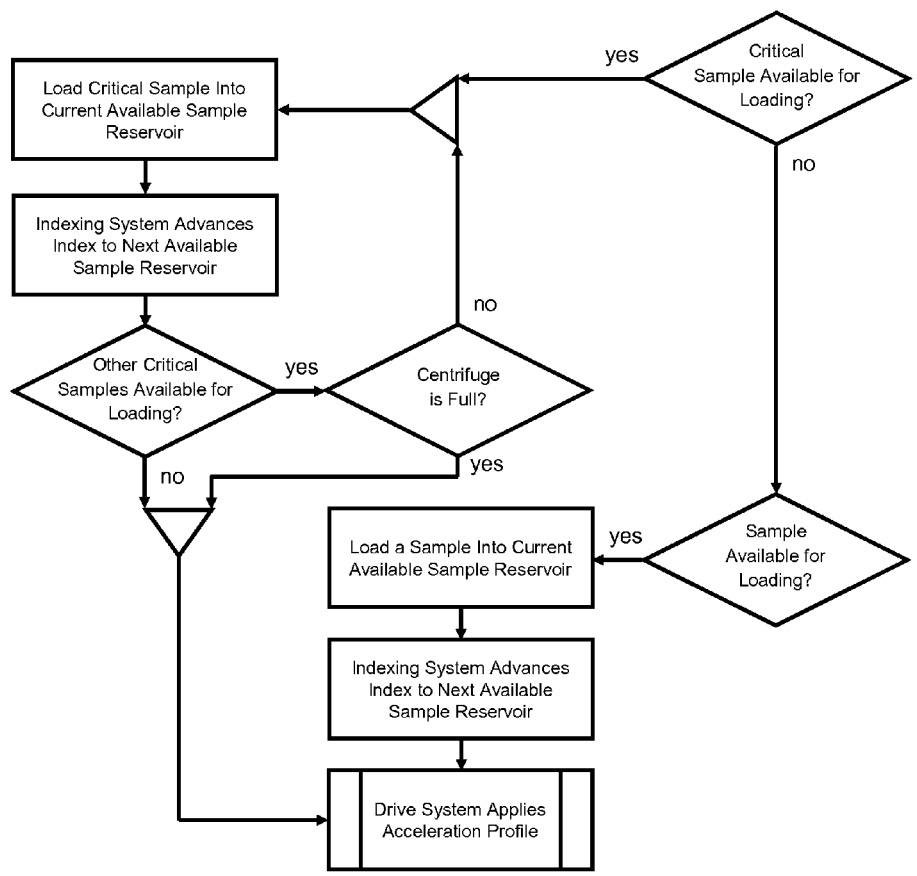
Figure 15:
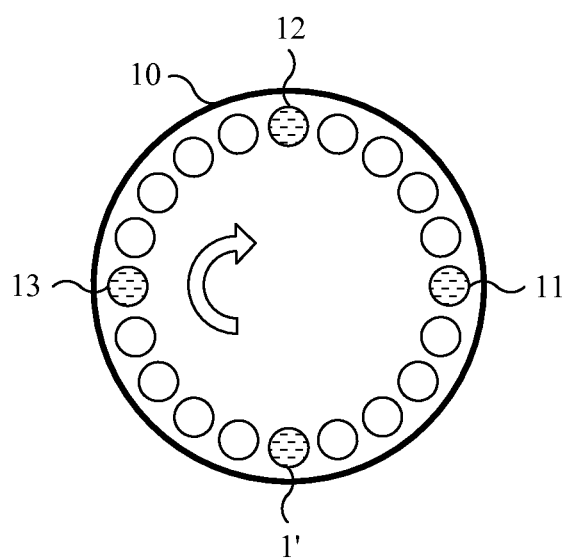
Figure 16:
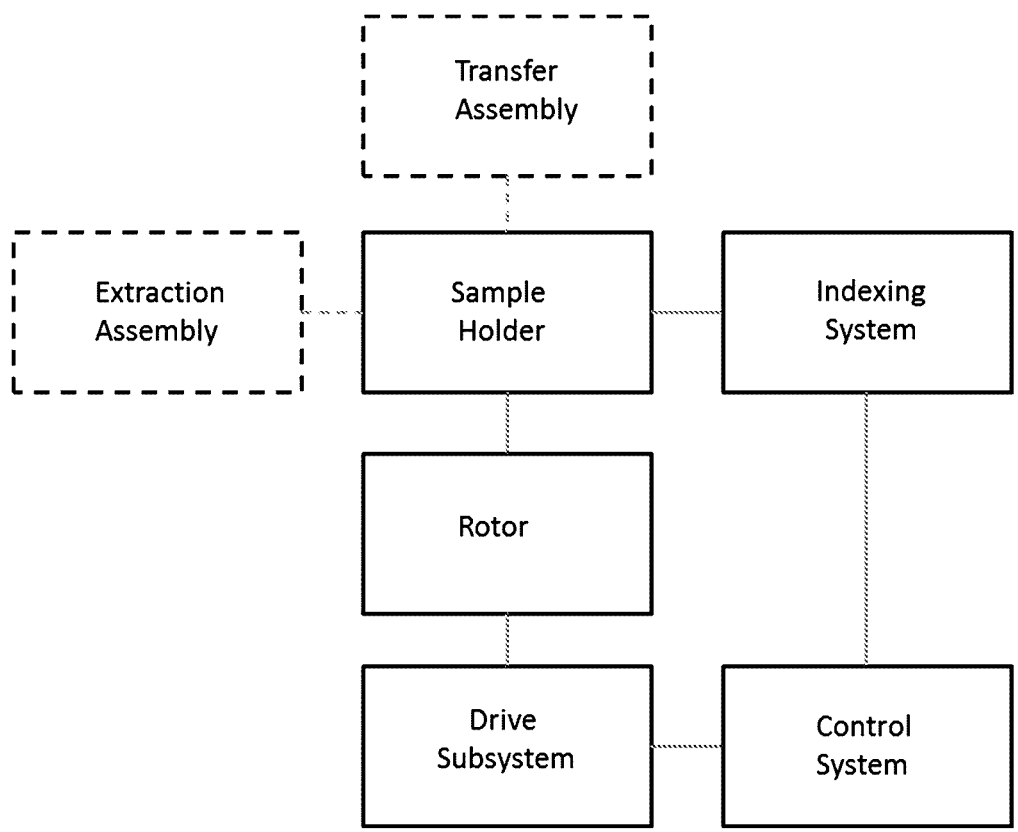

Having thus described the invention in general terms, reference will now be made to the accompanying drawings, which are not necessarily drawn to scale, and wherein:

FIG. 1 shows a graphical representation of how a centrifuge of the prior art achieves a desired total amount of force and time on a centrifuged sample;

FIG. 2 shows a graphical representation of how an exemplary embodiment of a sequential centrifuge of the present invention achieves a desired total amount of force and time on a centrifuged sample;

FIGS. 3A, 3B, 3C, and 3D are top plan views of a carousel used in certain embodiments of the inventive centrifuge showing four consecutive centrifugation sequences in an embodiment where a single sample is loaded in each centrifugation sequence in a position juxtaposed to a sample reservoir where a prior sample has been loaded;

FIGS. 4A, 4B, 4C, and 4D are top plan views of a carousel used in certain embodiments of the inventive centrifuge showing four consecutive centrifugation sequences in an embodiment where a single sample is loaded in each centrifugation sequence to maintain balance in the centrifuge;

FIG. 5 is a flowchart of an embodiment of the steps of the centrifugation sequence when a single sample is loaded in the centrifuge in each sequence;

FIG. 6 is a flowchart of another embodiment of the steps of the centrifugation sequence when a single sample is loaded in the centrifuge in each sequence;

FIG. 7 is a flowchart of an embodiment of the steps of a centrifugation cycle;

FIG. 8 is a flowchart of an embodiment of the steps of the centrifugation sequence for centrifuging a critical sample;

FIGS. 9A, 9B, and 9C are top plan views of a carousel used in certain embodiments of the inventive centrifuge showing three consecutive centrifugation sequences in an embodiment where one or more samples are loaded into the centrifuge during a centrifugation sequence in a position juxtaposed to a sample reservoir where a previous sample has been loaded;

FIG. 9D is a top plan view of a carousel used in certain embodiments of the inventive centrifuge showing an embodiment where there are no samples waiting to be loaded in a centrifugation sequence;

FIGS. 10A, 10B, and 10C are top plan views of a carousel used in certain embodiments of the inventive centrifuge showing one centrifugation sequence in an embodiment when three samples that are waiting to be loaded are loaded into the centrifuge in a position juxtaposed to the sample reservoir where a prior sample has been loaded;

FIGS. 11A, 11B, and 11C are top plan views of a carousel used in certain embodiments of the inventive centrifuge showing three consecutive centrifugation sequences in an embodiment where one or more samples are loaded into the centrifuge in a centrifugation sequence to maintain balance in the centrifuge;

FIG. 11D is a top plan view of a carousel used in certain embodiments of the inventive centrifuge showing an embodiment where there are no samples waiting to be loaded in a centrifugation sequence;

FIGS. 12A, 12B, and 12C are top plan views of a carousel used in certain embodiments of the inventive centrifuge showing one centrifugation sequence in an embodiment where three samples that are waiting to be loaded are loaded to maintain balance in the centrifuge;

FIG. 13 is a flowchart of an embodiment of the steps of the centrifugation sequence when all samples waiting to be loaded are loaded in the centrifuge in each sequence;

FIG. 14 is a flowchart of an embodiment showing the steps for determining whether there is a critical sample that is to be loaded in the centrifuged;

FIG. 15 is a top plan view of a carousel used in certain embodiments of the inventive centrifuge showing one centrifugation sequence in an embodiment where the indexing system chooses to load a plurality of samples that are waiting to be loaded to maintain balance in the centrifuge; and FIG. 16 is a schematic block drawing of various components of a sequential centrifuge in accordance with one embodiment of the present invention.

DETAILED DESCRIPTION OF THE INVENTION

The present invention now will be described more fully hereinafter with reference to the accompanying drawings, in which some, but not all embodiments of the inventions are shown. Preferred embodiments of the invention may be described, but this invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments of the invention are not to be interpreted in any way as limiting the invention.

Like numbers refer to like elements throughout. As further adopted herein, a number referencing a sample without a prime notation generally refers to the sample being subject to a single centrifugation sequence, a number referencing a sample with a single prime notation "'" generally refers to the sample being subject to a second centrifugation sequence, a number referencing a sample with a double prime notation "''" generally refers to the sample being subject to a third centrifugation sequence, and a number referencing a sample with a triple prime notation "'''" generally refers to the sample being subject to a fourth centrifugation sequence.

Many modifications and other embodiments of the inventions set forth herein will come to mind to one skilled in the art to which this inventions pertain having the benefit of the teachings presented in the descriptions herein and the associated drawings. Therefore, it is to be understood that the inventions are not to be limited to the specific embodiments disclosed and that modifications and other embodiments are intended to be included within the scope of the appended claims.

As used in the specification and in the appended claims, the singular forms "a", "an", and "the" include plural referents unless the context clearly indicates otherwise. For example, reference to "a sample" includes a plurality of such samples.

It will be understood that relative terms, such as "radially" or "circumferentially" or "bottom" or "top" or the like, may be used herein to describe one element's relationship to another element as illustrated in the Figures. It will be understood that relative terms are intended to encompass different orientations of the articles in addition to the orientation as illustrated in the Figures. It will be understood that such terms can be used to describe the relative positions of the element or elements of the invention and are not intended, unless the context clearly indicates otherwise, to be limiting.

Embodiments of the present invention are described herein with reference to various perspectives, including cross-sectional and perspective views that are schematic representations of idealized embodiments of the present invention. As a person having ordinary skill in the art to which this invention belongs would appreciate, variations from or modifications to the shapes as illustrated in the Figures are to be expected in practicing the invention. Such variations and/or modifications can be the result of manufacturing techniques, design considerations, and the like, and such variations are intended to be included herein within the scope of the present invention and as further set forth in the claims that follow. The articles of the present invention and their respective components illustrated in the Figures are not intended to illustrate the precise shape of the component of an article and are not intended to limit the scope of the present invention.

Although specific terms are employed herein, they are used in a generic and descriptive sense only and not for purposes of limitation. All terms, including technical and scientific terms, as used herein have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

The invention described herein relates to a sequential centrifuge. The sequential centrifuge is generally comprised of a centrifuge, the centrifuge having a drive subsystem, a rotor, and at least one sample holder; an indexing system for advancing an index from a current available sample reservoir in the centrifuge to a next available sample reservoir in the centrifuge; and a control system for performing a centrifugation sequence. Optionally, the sequential centrifuge may further comprise a transfer assembly for loading a sample into a sample reservoir of the at least one sample holder. Further, the sequential centrifuge may optionally comprise one or more extraction assemblies for removing a centrifuged sample that has reached a desired total amount of relative centrifugal force and time (total FT) from the centrifuge. The invention provides improvements over conventional centrifuges known in the art by reducing dwell time through reducing the amount of time the samples must wait before being processed, increasing system throughput by reducing or eliminating the idle time of the centrifuge, decreasing requirements for equipment footprint by reducing the size of the centrifuge and reducing the amount of area needed for sample preparation, improving precision of the analytical process by more accurately achieving a desired total FT applied to a sample, and allowing critical samples that need immediate processing to intervene in normal sample processing without a loss in efficiency of operation.

The term "total FT" as used herein means the sum of the integral of applied RCF in the time periods the RCF was applied to a given sample. Total FT is given by the formula:

$$\text{total } FT = \sum_{i=1}^{n} \int_{t_{i-1}}^{t_i} RCF_i \, dt.$$

Hence, the total FT for the acceleration cycle when the RCF represents a linear ramp function over a time period $t_0$ to $t_1$ to a target value $RCF_f$, a constant centrifugation cycle at $RCF_f$ between $t_1$ and $t_2$, and a linear ramp function of deceleration between $t_2$ and $t_3$ is given by the formula:

$$\text{total } FT_{sequence} = RCF_f \frac{(t_1 - t_0)}{2} + RCF_f(t_2 - t_1) + RCF_f \frac{(t_3 - t_2)}{2}.$$

When a sample is subjected to multiple sequences of acceleration, centrifugation, and deceleration, then the total FT is represented by a sum of the total FT for each of the sequences. As one skilled in the art can understand, there are many different possibilities for imparting a desired total FT to a sample and are not limited to this expressed embodiment given for the purpose of illustration.

Conventionally, centrifuges for processing discrete samples do so in a batch manner. I.e., an operator, or some other automated system, loads the samples into a sample holder. Centrifugation will not begin until a minimum number of samples are loaded in the sample holder. Hence, the samples that are loaded earlier will experience dwell time until the minimum requisite number of samples are loaded to begin centrifugation. Further, depending on the availability of the minimum requisite number of samples, the idle time, or time when the centrifuge is not in operation, can become quite large, particularly during those periods when samples do not become available very frequently. In addition to the underutilization of available equipment, the idle time further serves to increase the dwell time of samples that are available to be processed. The increased dwell time can lead to a loss of precision in the analytical process especially when a ratio of separated particles is critical to a sample analysis. Finally, the conventional batch processing of discrete samples does nothing to increase the speed of centrifuging critical samples that may periodically need to be processed. The inventive centrifuge as disclosed herein overcomes these problems as well as providing other advantages.

Discrete samples that require centrifugation before further analysis can be performed typically requires that a set force, as measured by RCF, be applied, and the set force be applied over a certain amount of time during centrifugation. Conventionally, after startup and before spinning down, centrifugation takes place over a substantially continuous time interval at a substantially constant RCF. FIG. 1 is a graphical representation of how a centrifuge of the prior art achieves a desired total amount of force and time on a centrifuged sample. The sample container 1 has a sample consisting of suspended heavy particles 2 and suspended light particles 3. The sample container 1 is subjected to one centrifugation sequence. This exemplary centrifugation is a density gradient centrifugation using a gradient medium 4. The centrifugation sequence has an acceleration cycle 5 to achieve a desired RCF in the centrifuge, a centrifugation cycle 6 that maintains the desired RCF for a certain amount of time, and a deceleration cycle 7 to bring the centrifuge to a stop.

FIG. 2 is a graphical representation of how an exemplary embodiment of a sequential centrifuge of the present invention achieves a desired total amount of force and time on a centrifuged sample. In this embodiment, the centrifugation is carried out in a series of four centrifugation sequences. In the first centrifugation sequence, sample container 1, containing suspended heavy particles 2 and suspended light particles 3, is centrifuged. This embodiment shows the use of a density gradient medium 4. The first centrifugation sequence has an acceleration cycle 5 to achieve a desired RCF in the centrifuge; a centrifugation cycle 6 that maintains the desired RCF for, in this embodiment, a set period of time; and a deceleration cycle 7 to bring the centrifuge to a stop. Since, the first centrifugation sequence will not have been sufficient to achieve the desired total amount of force and time for the sample, the same sample container 1' with suspended heavy particles 2' and suspended light particles 3', now at different positions within the sample container 1' due to the first centrifugation sequence, will undergo a second centrifugation sequence. The second centrifugation sequence has an acceleration cycle 5' to achieve a desired RCF in the centrifuge; a centrifugation cycle 6' that maintains the desired RCF for, in this embodiment, a set period of time; and a deceleration cycle 7' to bring the centrifuge to a stop. The same sample container 1", but in a third centrifugation sequence, will continue to separate suspended heavy particles 2" and suspended light particles 3" by subjecting the sample container to an acceleration cycle 5" to achieve a desired RCF in the centrifuge; a centrifugation cycle 6" that maintains the desired RCF for, in this embodiment, a set period of time; and a deceleration cycle 7" to bring the centrifuge to a stop. Finally, the same sample container 1''', but in a fourth centrifugation sequence, will continue to separate suspended heavy particles 2''' and suspended light particles 3''' by subjecting the sample container to an acceleration cycle 5''' to achieve a desired RCF in the centrifuge; a centrifugation cycle 6''' that maintains the desired RCF for, in this embodiment, a set period of time; and a deceleration cycle 7''' to bring the centrifuge to a stop. The cumulative total of force and time applied in each of these four sequential centrifugation sequences can be substantially the same as the total FT applied in the conventional batch process. I.e., $$\sum_{i=5}^{7} \int RCF_i^{conv} dt \cong$$

$$\sum_{i=5}^{7} \left( RCF_i^{sequ} dt + \int RCF_{i'}^{sequ} dt + \int RCF_{i''}^{sequ} dt + \int RCF_{i'''}^{sequ} dt \right)$$

where $\int RCF_i/dt$ represents the total FT applied in any step i. As one skilled in the art can understand, there are many different possibilities for the number of centrifugation sequences that are part of a series for centrifuging a sample and are not limited to this expressed embodiment given for the purpose of illustration.

While this illustration is representative of merely one sample as it progresses through multiple centrifugation sequences, the true advantage of the inventive sequential centrifuge is its ability to process other samples as it continues through a multiplicity of cycles. Each time the centrifuge stops, at least one other sample, if available, can be introduced to the centrifuge for processing.

The phrases "sample loading," "loading a sample," "sample is loaded," and variations thereof as used interchangeably herein mean to place a sample into a centrifuge. As understood by a person having skill in the art, there are a variety of means to accomplish loading a sample into the centrifuge. A non-limiting example of sample loading can include a sample transfer system that removes a sample from a container vial and dispenses the sample into a sample container in the centrifuge. Such a sample transfer system can be accomplished by a variety of systems known in the art. An example of a sample transfer system includes, but is not limited to, an aspiration system and an injection system. Sample loading can include placing a sample container comprising the sample into the centrifuge. As further disclosed herein, the sample may be placed by a manual system and/or procedure, an automated system and/or procedure, and any combination thereof.

The phrase "configured to," "configured for", and variations thereof are used interchangeably herein to mean to provide the inventive device with a capability to perform a various, stated purpose. Such a capability can be achieved by, for example, the addition of a needed component, modification of an existing component, rearrangement of components, configuration of a control system, configuration of a master controller, and any combination thereof.

Figure 3A:
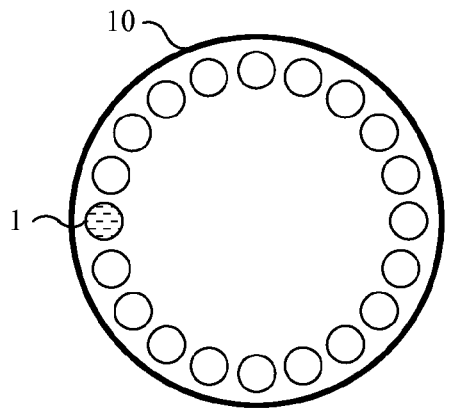
Figure 3B:
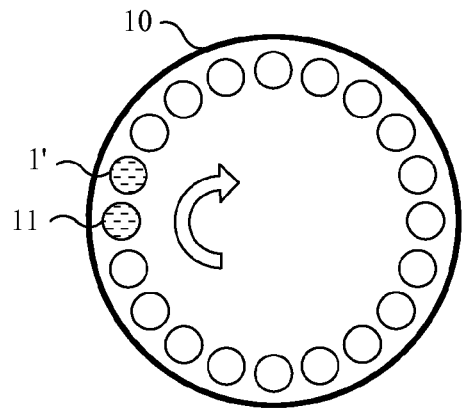
Figure 3C:
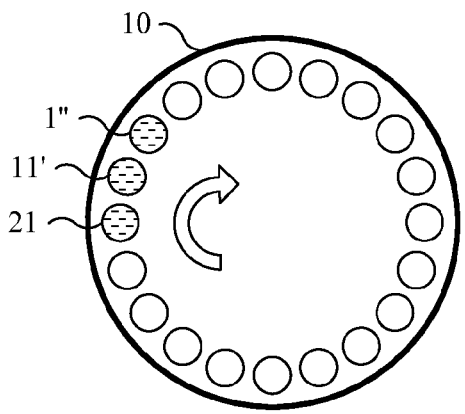
Figure 3D:
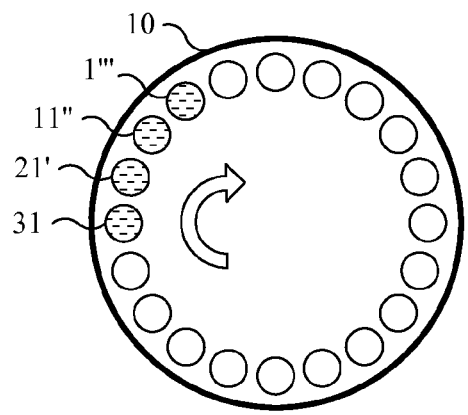

FIG. 3A is a top plan view of a carousel, used in certain embodiments of the inventive sequential centrifuge, showing where a sample is loaded into a first sample reservoir 1 for processing in a first centrifugation sequence. After loading the sample, the centrifugation sequence continues through an acceleration cycle, a centrifugation cycle, and a deceleration cycle. The indexing system advances an index to a next available sample reservoir identifying where the next sample is to be loaded. In this embodiment, the indexing system is configured to advance the index to a next available sample reservoir that is in a position juxtaposed to the current available sample reservoir that has just been loaded with a sample. After coming to a stop, as shown in FIG. 3B, a sample is loaded into a second sample reservoir 11 in a position juxtaposed to the first sample reservoir 1' whose sample remains in the centrifuge for the next centrifugation sequence that includes an acceleration cycle, centrifugation cycle, and a deceleration cycle. As shown in FIG. 3C, when the centrifuge comes to a stop after completing the second cycle, a sample is loaded into a third sample reservoir 21 in a position juxtaposed to the second sample reservoir 11' whose sample remains in the centrifuge along with the sample of the first sample reservoir 1" for a third centrifugation sequence that includes an acceleration cycle, centrifugation cycle, and a deceleration cycle. As shown in FIG. 3D, when the centrifuge comes to a stop after completing another centrifugation sequence, a sample is loaded into a fourth sample reservoir 31 in a position juxtaposed to the third sample reservoir 21' containing a sample remaining in the centrifuge for a second centrifugation sequence. Also remaining in the centrifuge are the sample in the second sample reservoir 11" undergoing a third centrifugation sequence and the sample in the first sample reservoir 1'" undergoing a fourth centrifugation sequence.

Any centrifuged sample that reaches its desired total FT at the conclusion of a centrifugation sequence will be removed from the centrifuge. The sample reservoir corresponding to the centrifuged sample that is removed can become available for loading another sample. Of course, the preference for when the available sample reservoir is used is determined by the indexing system and its corresponding configuration as further disclosed herein. In another embodiment of the invention, the sample reservoir may not become immediately available for loading another sample once a centrifuged sample is removed. For example, in these embodiments, it may be necessary to first clean the sample reservoir depending on the design of the sample reservoir as further disclosed herein. In other embodiments, it may be necessary to prepare the sample reservoir such as with, for example, at least one gradient medium depending on the type of centrifugation being performed as also disclosed herein.

A "sample reservoir," as used herein, can mean, for example, among other things, a socket for holding a sample container. In an embodiment of the invention, the sample reservoir comprises a sample container and a transfer system of the inventive centrifuge dispenses the sample into the sample container. In another embodiment of the invention, the sample comprises a sample container and the sample container holding the sample is manually placed into the socket of the sample reservoir. In another embodiment of the invention, a sample container holding the sample can be placed in the socket of the sample reservoir by an automated system. In still other embodiments of the invention, a sample container holding the sample can be placed in the socket of the sample reservoir by a combination of manually and automatically loading the sample container in the centrifuge. In one embodiment, the automated system for placing a sample container in the centrifuge comprises a robotic arm. In another embodiment, the automated system for placing a sample container in the centrifuge comprises a system for loading a sample container into a sample holder, conveying the sample holder to the centrifuge, and detachably affixing the sample holder to the rotor of the centrifuge. Indeed, any apparatus, method, and/or procedure known in the art may be used to accomplish loading a sample into a sample reservoir.

In one embodiment of the invention, the sample holder is a tub-shaped bowel. In another embodiment of the invention, the sample holder is a carousel. In yet another embodiment of the invention, the sample holder is a bucket. In still another embodiment of the invention, there are a plurality of samples holders with any sample holder of the plurality of sample holders selected from the group consisting of a tub-shaped bowel, a carousel, and a bucket. Indeed, the sample holder can be any device or apparatus known in the art.

Examples of manufacturers whose centrifuges could be used in the invention described herein include, but are not limited to: BD (Becton, Dickinson, and Company) Clay Adams Brand centrifuges (Franklin Lakes, N.J. USA); Beckman Coulter (Fullerton, Calif. USA); Drucker Company (Philipsburg, Pa. USA); and Hamilton Bell Co., Inc. (Montvale, N.J. USA).

In one embodiment of the invention, the extraction system that removes a centrifuged sample that has reached its desired total FT may aspirate the sample from the sample container. In another embodiment, the extraction system may comprise a plurality of aspiration stages for removing more than one layer from the centrifuged sample. In another embodiment of the invention, the sample container can be replaced with a clean sample container. In certain embodiments of the invention, the clean sample container comprises a gradient medium prior to loading the sample container into the centrifuge. In other embodiments, a gradient medium is dispensed into the clean sample container after the sample container has been placed into the centrifuge. In yet other embodiments, the clean sample container comprises a gradient medium prior to loading and either the same or at least one other gradient medium is dispensed into the clean sample container after it has been loaded into the centrifuge. In other embodiments of the invention, the used sample container may be cleaned while it remains in the centrifuge otherwise known as cleaned in place. In another embodiment, the used sample container that has been cleaned in place may optionally be loaded with at least one gradient medium if needed.

In another embodiment of the invention, the extraction system comprises manually removing the sample container from the centrifuge. In yet other embodiments of the invention, an automated system removes the sample container from the centrifuge. In still other embodiments of the invention, the extraction system comprises a combination of manually and automatically removing the sample container from the centrifuge. In one embodiment, an automated system for removing a sample container from the centrifuge comprises a robotic arm. In another embodiment, the automated system for removing a sample container from the centrifuge comprises detaching the sample holder from the rotor of the centrifuge, conveying the sample holder to an unloading station, and unloading a sample container from the sample holder. Indeed, any apparatus, method, and/or procedure known in the art may be used as an extraction system.

Figure 4A:
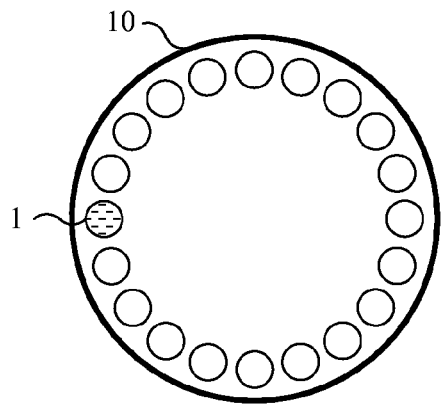
Figure 4B:
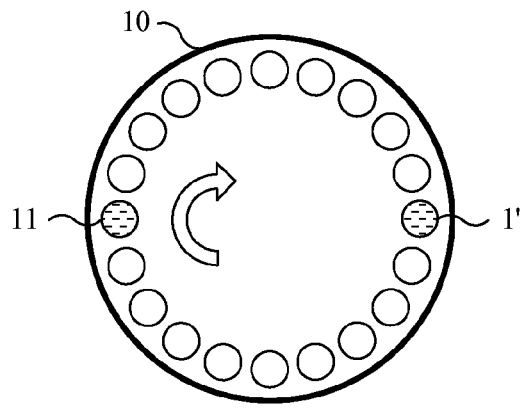
Figure 4C:
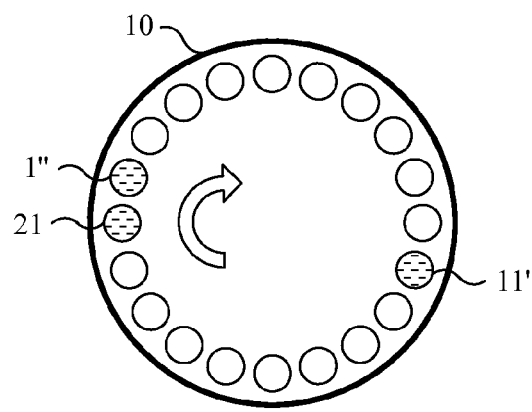
Figure 4D:
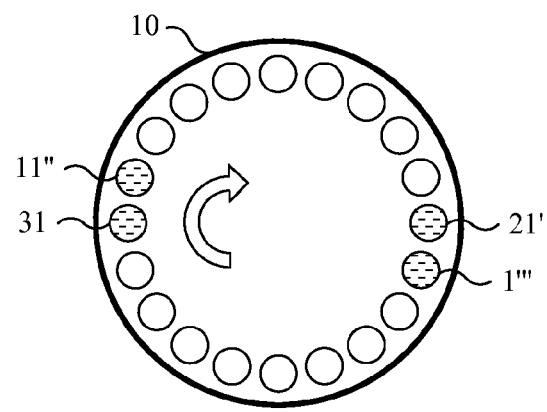

As presented earlier, FIG. 4A is a top plan view of a carousel, used in certain embodiments of the inventive sequential centrifuge, showing that a sample is loaded into a first sample reservoir 1 for processing in a first centrifugation sequence. However, in this embodiment, the indexing system is configured to advance the index to a next available sample reservoir that needs to be loaded in order to maintain balance in the centrifuge. FIG. 4B shows that after the centrifuge completes its acceleration cycle, centrifugation cycle, and deceleration cycle, a sample is loaded into a second sample reservoir 11 identified by the indexing system as needed to maintain balance in the centrifuge. FIG. 4C shows that following completion of the next acceleration cycle, centrifugation cycle, and deceleration cycle, a sample is loaded into a third sample reservoir 21 identified by the indexing system as needed to maintain balance in the centrifuge. FIG. 4D shows that following completion of the next acceleration cycle, centrifugation cycle, and deceleration cycle, a sample is loaded into a fourth sample reservoir 31 identified by the indexing system as needed to maintain balance in the centrifuge. The arrangements shown in FIGS. 4A, 4B, 4C, and 4D are merely exemplary of this embodiment. In other embodiments, the indexing system may choose to load samples in a different configuration in order to maintain balance in the centrifuge.

The embodiments in FIGS. 3 and 4 are illustrative of how a single sample is loaded into a sample reservoir at every centrifugation sequence. In the event a sample is not available for loading after the centrifuge has stopped to remove a centrifuged sample that has achieve a desired total FT, the control system can be configured to continue the next centrifugation cycle without sample loading as long as there are samples remaining in the centrifuge that have not reached a desired total FT. FIG. 5 is a flowchart of an embodiment showing how, if a sample is available for loading, it will be loaded into the current available sample reservoir and the indexing system will advance the index to the next available sample reservoir. If a sample is not yet available for loading, these steps can be bypassed and the acceleration cycle can begin as long as there are other samples remaining in the centrifuge. Optionally, the control system may be configured to wait a certain period of time before proceeding in the event a sample does become available for loading (not shown). After completion of the acceleration cycle, the centrifugation cycle, and the deceleration cycle, any centrifuged sample that has achieved the desired total FT is removed from the centrifuge. Optionally, the sequential centrifuge can be configured to continue the centrifugation cycle in the event a sample is not yet available for loading as long as there is no centrifuged sample in the centrifuge that has achieved the desired total FT. One example of this embodiment is shown in the flowchart of FIG. 6. As shown in both FIGS. 5 and 6, the system continues to cycle through the centrifugation sequence.

In other embodiments of the invention, the centrifugation sequence can be configured to continue the centrifugation cycle until an event occurs. In one embodiment of the invention, the event includes at least one of a minimum period of time has elapsed, a preset period of time has elapsed, a preset number of samples have become available for loading, and a desired total FT is achieved by any one centrifuged sample. In certain embodiments of the invention, the present number of samples is set to one sample. In other embodiments of the invention, the preset number of samples is set to more than one sample. FIG. 7 is a flowchart of an embodiment of the invention showing the steps of a centrifugation cycle. Of course, if there are currently no remaining available reservoirs in which to load a sample, then the centrifugation cycle can be continued until a desired total FT is achieved by at least one centrifuged sample in order to make a reservoir available for a sample that is available for loading in the next centrifugation sequence (not shown). As used herein, "centrifugation cycle" means the cycle following an acceleration cycle and preceding a deceleration cycle in the centrifugation sequence. The centrifugation cycle can be configured to proceed at a varying RCF. Preferably, the centrifugation cycle will be configured to proceed at a preset RCF that is substantially constant.

FIG. 8 is a flowchart of an embodiment of the invention showing the steps of the centrifugation sequence for processing a critical sample. The ingenious design of the present invention allows critical sample processing when processing a single sample in each centrifugation sequence to be easily implemented. The critical sample merely needs to be placed in the front of the sample processing queue. "Sample processing queue" as used herein means samples that are waiting to be loaded into the centrifuge. However, as shown in FIG. 8, the control system must consider additional elements to ensure the centrifuge does not stop for a subsequent sample unless the subsequent sample is a critical sample, the desired total FT has been achieved for any sample in the centrifuge, the desired total FT has been achieved for the critical sample in the centrifuge, and any combination thereof.

In the event samples have varying degrees of priority, the samples in the sample processing queue can be arranged in order of descending priority with the highest priority sample being centrifuged first. The sample processing queue can be arranged manually, automatically, or by an indexing system similar to the indexing system of the inventive device. Any sample arrangement method known in the art may be used.

In addition to loading only one sample in each centrifugation sequence, the sequential centrifuge can be configured to load more than one sample or to even load as many samples that are waiting to be loaded subject to available sample reservoirs in the centrifuge. As presented earlier, FIG. 9A is a top plan view of a carousel, used in certain embodiments of the inventive sequential centrifuge, showing that a sample is loaded into a first sample reservoir 1 for processing in a first centrifugation sequence. Because, in this example, only one sample is available for loading in this centrifugation sequence, the centrifuge continues to perform an acceleration cycle, a centrifugation cycle, and a deceleration cycle. However, in this example embodiment, while the first sample proceeds through the centrifugation sequence, an additional three samples become available for loading. In this embodiment of the invention, the indexing system is configured to advance the index to a next available reservoir that is in a position juxtaposed to the current available reservoir that has just been loaded with a sample. Therefore, the next three samples now available for loading become loaded into a second sample reservoir 11, a third sample reservoir 12, and a fourth sample reservoir 13 as presented in FIG. 9B. In fact, sample loading and indexing proceed as before with the exception that the other cycles of the centrifugation sequence are not executed until all the samples that are waiting or, optionally, a maximum preset number of samples that are waiting have been loaded up to the limit of available sample reservoirs remaining in the centrifuge. An embodiment of a loading scheme when three samples that are waiting to be loaded are loaded is shown in FIGS. 10A, 10B, and 10C.

As shown in FIG. 10A, the first sample that is waiting is loaded into a second sample reservoir 11 in a position juxtaposed to the first sample reservoir 1'. The indexing system, configured to index to the next available sample reservoir that is in a position juxtaposed to the current available sample reservoir, provides that the second sample that is waiting be loaded into a third sample reservoir 12 in a position juxtaposed to the second sample reservoir 11 as shown in FIG. 10B. As FIG. 10C shows, when either only three samples are waiting or the system has been configured to accept a maximum of three samples at a time, the indexing system provides that the third sample is to be loaded into a fourth sample reservoir 13 in a position juxtaposed to the third sample reservoir 12. After at least one of all waiting samples have been loaded, the maximum number of samples have been loaded, and no sample reservoirs are available in the centrifuge, the centrifugation sequence proceeds with the acceleration cycle, the centrifugation cycle, and the deceleration cycle. After checking for whether any samples have reached the desired total FT and unloading the same, the system then loads an additional two samples that, in this exemplary embodiment, have become available for loading. The first sample is loaded into the fifth sample reservoir 21 in a position juxtaposed to the fourth sample reservoir 13' and the second sample is loaded into the sixth sample reservoir 22 in a position juxtaposed to the fifth sample reservoir 21 pursuant to the index provided by the indexing system as configured in this embodiment. This loading scheme is shown in FIG. 9C.

As shown in FIG. 9D, when there are no samples waiting to be loaded, the centrifugation sequence can continue the centrifugation cycle without stopping for sample loading, similar to the embodiment shown in certain relevant portions of the flowchart in FIG. 6, as long as there are centrifuged samples in the centrifuge that have not reached the desired total FT. Alternatively, the system may be configured to continue with the deceleration cycle and wait for the next sample that becomes available for loading. In this embodiment of the invention, the time to wait for the next sample may be configured not to exceed a certain period of time.

As presented earlier, FIG. 11A is a top plan view of a carousel, used in certain embodiments of the inventive sequential centrifuge, showing where a sample is loaded into a first sample reservoir 1 for processing in a first centrifugation sequence. Because, in this example, only one sample is available for loading in this centrifugation sequence, the centrifuge continues to proceed through an acceleration cycle, a centrifugation cycle, and a deceleration cycle. However, in this example embodiment, while the first sample proceeds through the centrifugation sequence, an additional three samples become available for loading. In this embodiment, the indexing system is configured to advance the index to a next available sample reservoir that needs to be filled in order to maintain balance in the centrifuge. Therefore, the next three samples now available for loading become loaded into a second sample reservoir 11, a third sample reservoir 12, and a fourth sample reservoir 13 as presented in FIG. 11B. In fact, sample loading and indexing proceed as before with the exception that the other cycles of the centrifugation sequence are not executed until all the samples that are waiting or, optionally, a maximum preset number of samples that are waiting have been loaded up to the limit of remaining available sample reservoirs in the centrifuge. An embodiment of a loading scheme for three samples that are waiting is shown in FIGS. 12A, 12B, and 12C.

As shown in FIG. 12A, the first sample that is waiting is loaded into a second sample reservoir 11 that is needed to maintain balance in the centrifuge. The indexing system, configured to index to the next available sample reservoir that is needed to be loaded with a sample to maintain balance in the centrifuge, provides that the second sample that is waiting be loaded into a third sample reservoir 12 as shown in FIG. 12B. As FIG. 12C shows, when either only three samples are waiting to be loaded or the system has been configured to load a maximum of three samples at a time, the indexing system provides that the third sample be loaded into a fourth sample reservoir 13, which is chosen by the indexing system to maintain balance in the centrifuge. After at least one of all waiting samples have been loaded, the maximum number of samples has been loaded, and no sample reservoirs are available in the centrifuge, the centrifugation sequence proceeds with the acceleration cycle, the centrifugation cycle, and the deceleration cycle. After checking for whether any samples have reached the desired total FT and unloading the same, the system then loads an additional two samples that, in this exemplary embodiment, are waiting to be loaded. The first sample is loaded into the fifth sample reservoir 21 chosen by the indexing system to maintain balance in the centrifuge and the second sample is loaded into the sixth sample reservoir 22 again chosen by the indexing system to maintain balance in the centrifuge. This loading scheme is shown in FIG. 11C.

As shown in FIG. 11D, when there are no samples waiting to be loaded, the centrifugation sequence can continue the centrifugation cycle without stopping for sample loading, similar to the embodiment shown in certain relevant portions of the flowchart in FIG. 6, as long as there are no centrifuged samples in the centrifuge that have reached the desired total FT. Alternatively, the system may be configured to continue with the deceleration cycle and wait for the next sample that becomes available to be loaded. In this embodiment of the invention, the time to wait for the next sample may be configured not to exceed a certain period of time.

The loading arrangements shown in FIGS. 11A, 11B, 11C, 11D, 12A, 12B, and 12C are merely exemplary of certain embodiments of the invention. In other embodiments, the indexing system may choose to load samples in a different configuration in order to maintain balance in the centrifuge.

The flowchart in FIG. 13 shows the steps of an embodiment of the invention when all samples in the queue are loaded into the centrifuge in each centrifugation sequence. In this embodiment, as long as there are samples waiting to be loaded and there is room available in the centrifuge, sampling loading and indexing will continue. As further disclosed herein, the number of samples loaded in each centrifugation sequence can be limited to a maximum number of samples to be loaded (not shown). The centrifugation sequence then proceeds through an acceleration cycle, a centrifugation cycle, and a deceleration cycle. Optionally, the centrifugation cycle can be configured to continue if there are no samples waiting to be loaded and there are no centrifuged samples that have reached a desired total FT similar to certain representative steps shown in the flowchart of FIG. 6. The centrifugation cycle may continue until any number of a set of rules has executed, similar to the steps shown in FIG. 7. Alternatively, the centrifugation sequence may be configured to continue for a preset period of time as shown in the embodiment in FIG. 5. Of course, if there are currently no remaining available reservoirs in which to load a sample, the centrifugation cycle can be configured to continue until a desired total FT is achieved by at least one centrifuged sample in order to make a sample reservoir available for a sample that is available for loading at the start of the next centrifugation sequence. Any number of different configurations for the centrifugation cycle can be envisioned given the benefit of this disclosure. Such embodiments are intended to be part of this disclosure. After the deceleration cycle ends, the system checks to see if any centrifuged sample has reached a desired total FT and, if so, the centrifuged sample is unloaded as described herein. The centrifugation sequence begins again by loading samples that are available for loading or, if none are available, the centrifugation sequence can optionally proceed to an acceleration cycle if centrifuged samples remain in the centrifuge that have not achieve a desired total FT.

In the circumstance when a critical sample becomes available for loading in the embodiments of the invention when multiple samples can be loaded during a centrifugation sequence, the critical sample should be loaded without loading any additional samples unless, perhaps, these additional samples are also identified as critical. FIG. 14 is a flowchart of an embodiment of the steps in determining whether there are one or more critical samples that should be processed over other samples waiting to be centrifuged. If one or more critical samples are identified and loaded in the centrifuge, then the acceleration cycle, the centrifugation cycle, and the deceleration cycle can proceed similar to the embodiment disclosed in the flowchart of FIG. 8. According to this embodiment, the centrifuge does not stop for a subsequent sample unless at least one of the subsequent samples is a critical sample, the desired total FT has been achieved for any sample in the centrifuge, and the desired total FT has been achieved for the critical sample in the centrifuge. In other embodiments of the invention, the determination of which critical sample is to be first loaded and whether the centrifuge that is processing a critical sample stops in favor of loading another critical sample that is waiting to be loaded can be determined by a priority ranking of the critical samples.

An embodiment of the invention provides that the acceleration cycle profile will be a ramp profile. "Ramp profile," as used herein, means the centrifuge starts from a starting RCF and rises substantially linearly over a given period of time until the centrifuge is operating at a target RCF. In the case of spinning up the centrifuge from a stopped state, the starting RCF is zero. Other acceleration cycle profiles can be configured. Generally, concave upward profiles allow for slower starting acceleration rates but subsequently progressing to faster acceleration rates, while concave downward profiles allow for faster starting acceleration rates but subsequently progressing to slower acceleration rates. Concave upward and downward profiles may be used alone or in varying combinations. In particular, a combination beginning with a concave upward profile followed by a concave downward profile, similar to an S-shape, allows the acceleration of the centrifuge to start out slowly, begin to rise asymptotically to some point just less than the target RCF, and slow until reaching the target RCF. Any number of configurations are possible that can include linear shaped profiles, curved profiles, and combinations thereof. Preferably, an acceleration cycle profile is selected such that resuspension of already settled particles in samples that have been centrifuged in prior centrifugation sequences is sufficiently minimized if not avoided entirely.

Deceleration cycle profiles can similarly be a ramped profile where the RCF is reduced substantially linearly over a given time period. Other deceleration cycle profiles can be configured. It is possible to achieve mostly any profile particularly when the centrifuge is equipped with a braking system. Generally, concave downward profiles allow for slower starting deceleration rates but subsequently progressing to faster deceleration rates, while concave upward profiles allow for faster starting deceleration rates but subsequently progressing to slower deceleration rates. Concave upward and downward profiles may be used alone or in varying combinations. In particular, a combination beginning with a concave downward profile followed by a concave upward profile, similar to an S-shape, allows deceleration to start out slowly, begin to drop asymptotically to some point just before bringing the centrifuge to a stop, and slowing until the centrifuge reaches a stopped state. Any number of deceleration cycle profiles are possible and are intended to be a part of this disclosure. Such profiles can include linear shaped profiles, curved profiles, and combinations thereof. Preferably, a deceleration cycle profile is selected such that resuspension of already settled particles in the centrifuged samples is sufficiently minimized if not avoided entirely.

The flowcharts of FIGS. 5, 6, 8, and 13 show an indexing system that advances the index to a next available sample reservoir. The indexing system may choose the next available sample reservoir to be a sample reservoir in a position juxtaposed to the prior sample reservoir that has been loaded with a sample. Alternatively, the indexing system may choose the next available sample reservoir as a sample reservoir needed to maintain balance in the centrifuge. The indexing system may use, to its advantage, the configuration of the system in determining how to best load sample containers within the centrifuge. In a non-limiting example, FIG. 15 shows an embodiment when there are three samples waiting to be loaded into the centrifuge, the indexing system will choose to load the first of these three samples in a second sample reservoir 11, the second of these three samples in a third sample reservoir 12, and the third of these three samples in a fourth sample reservoir 13 for the purposes of maintaining balance in the centrifuge in relation to a sample reservoir 1' that already contains a sample from a prior sequence. In other embodiments of the invention, the indexing system can be configured to load a sample in any geometric configuration. Other loading configurations, as perceived by persons having ordinary skill in the art with the benefit of this disclosure, are intended to be incorporated into this disclosure.

While the indexing system and its judicious selection of sample positions in the centrifuge can play a significant role in maintaining balance in the centrifuge, other embodiments of the invention involve designing the sequential centrifuge such that it can be balanced, either manually and/or automatically, when the samples are loaded in the centrifuge. Yet other embodiments of the invention involve designing the sequential centrifuge such that it can become automatically balanced when samples have been loaded asymmetrically within the centrifuge and/or the centrifuge experiences dynamic imbalances. The centrifuge may be designed with larger rotor bearings or may have upper and lower bearing mounts that are capable of substantial movement in the horizontal plane for self-balancing in order to overcome some degree of imbalance. More extreme imbalance conditions in the centrifuge can be detected by equipping the centrifuge with an accelerometer for measuring vibration or oscillations in the rotor caused by an imbalance condition. This information can be relayed to the control system allowing the control system to work with the indexing system to compensate for such imbalance conditions in the next sample loading cycle. In still other embodiments, automated features may be incorporated into the centrifuge to bring the centrifuge back into balance during a centrifugation sequence when such a situation is detected. In still other embodiments, automated features are incorporated into the centrifuge and the control system simultaneously works with the indexing system to compensate for an imbalance condition.

In certain embodiments of the invention, when an imbalance condition is detected, the system is configured to automatically compensate the amount of time the sample needs in the sequential centrifuge to achieve the desired total FT for each of the samples processed during the imbalance condition.

Having the benefit of this disclosure, a person skilled in the art can contemplate other loading profiles to meet any number of objectives. Such objectives include, but are not limited to, spatial and/or geometric distribution of samples in the centrifuge, with some representative embodiments as disclosed herein for purposes of illustration; organization by sample type; any configuration to maintain balance in the centrifuge, some representative embodiments as disclosed herein for purposes of illustration; design considerations of the centrifuge and ancillary processing facilities; and any combination thereof. In certain embodiments, the indexing system may index sample reservoirs in other sample holders when the centrifuge comprises a plurality of holders. In yet other embodiments, the indexing system may index sample reservoirs in other sequential centrifuges when more than one sequential centrifuge is in operation. The choice for such a selection may be for any reason as disclosed herein.

Another aspect of the invention are methods for sequentially centrifuging a plurality of samples. In one embodiment of the invention, the method for sequentially centrifuging a plurality of samples includes the steps of providing a centrifuge comprising a drive subsystem, a rotor coupled to the drive subsystem, and at least one sample holder affixed to the rotor, the at least one sample holder having a plurality of sample reservoirs for holding a sample; loading a first sample into a current available sample reservoir; indexing to a next available sample reservoir; accelerating to achieve a preset RCF; maintaining the preset RCF for an amount of time less than the amount of time needed to achieve a desired total FT for the first sample; decelerating to the bring the centrifuge to a stop; repeating the loading and indexing steps for other samples and the accelerating, maintaining, and decelerating steps until the first sample has achieved the desired total FT; and removing the first sample from the centrifuge.

In another embodiment of the invention, the method for sequentially centrifuging a plurality of samples includes the steps of providing a centrifuge comprising a drive subsystem, a rotor coupled to the drive subsystem, and at least one sample holder affixed to the rotor, the at least one sample holder having a plurality of sample reservoirs for holding a sample; loading a sample into a current available sample reservoir; indexing to a next available sample reservoir; accelerating to achieve a preset RCF; maintaining the preset RCF until an event occurs, the event selected from the group consisting of a minimum period of time has elapsed, a preset period of time has elapsed, a preset number of samples have become available for loading, a desired total FT is achieved by any one centrifuged sample, and combinations thereof; decelerating to the bring the centrifuge to a stop; and removing a centrifuged sample that has achieved the desired total FT.

In another embodiment of the invention, the method for sequentially centrifuging a plurality of samples further comprises the step of repeating the loading, indexing, accelerating, maintaining, decelerating, and removing steps so that each sample of the plurality of samples achieves the desired total FT.

All publications mentioned herein, including patents, patent applications, and journal articles are incorporated herein by reference in their entireties including the references cited therein, which are also incorporated herein by reference. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated by those skilled in the art that changes could be made to the embodiments described herein without departing from the broad inventive concept thereof. Therefore, it is understood that this invention is not limited to the particular embodiments disclosed, but it is intended to cover modifications within the spirit and scope of the present invention as defined by the appended claims.

That which is claimed:

1. A method for sequentially centrifuging a plurality of samples comprising the steps of:
    providing a centrifuge comprising a drive subsystem, a rotor coupled to the drive subsystem, and at least one sample holder affixed to the rotor, the at least one sample holder having a plurality of sample reservoirs for holding a sample;
    loading a first sample into a current available sample reservoir;
    indexing to a next available sample reservoir;
    accelerating to achieve a preset relative centrifugal force (RCF);
    maintaining the preset RCF for an amount of time less than the amount of time needed to achieve a desired total FT for the first sample;
    decelerating to bring the centrifuge to a stop;
    repeating the loading and indexing steps for at least one other sample and the accelerating, maintaining, and decelerating steps until the first sample has achieved the desired total FT; and
    removing the first sample from the centrifuge.

2. The method according to claim 1, wherein the maintaining step additionally comprises maintaining the preset RCF until an event occurs, the event selected from the group consisting of a minimum period of time has elapsed, a preset period of time has elapsed, a preset number of samples have become available for loading, a desired total FT is achieved by any one centrifuged sample, and combinations thereof.

3. The method according to claim 2, further comprising the step of repeating the loading, indexing, accelerating, maintaining, decelerating, and removing steps so that each sample of the plurality of samples achieves the desired total FT.

4. The method according to claim 1, wherein the first sample is a critical sample.

5. The method according to claim 4, additionally comprising the step of placing the critical sample in front of a sample processing queue.

6. The method according to claim 5, wherein the maintaining step additionally comprises maintaining the preset RCF until an event occurs, the event selected from the group consisting of another critical sample is available at the front of the sample processing queue, the desired total FT is achieved by any one centrifuged sample, the desired total FT is achieved by the critical sample, and combinations thereof.

7. The method according to claim 1, wherein the next available sample reservoir is chosen in order to maintain balance in the centrifuge.

* * * * *